US009427468B2

(12) United States Patent
Cheung et al.

(10) Patent No.: US 9,427,468 B2
(45) Date of Patent: Aug. 30, 2016

(54) **COMPOSITIONS AND METHODS FOR DIAGNOSING AND TREATING COMMUNITY-ACQUIRED METHICILLIN-RESISTANT *STAPHYLOCOCCUS AUREUS***

(75) Inventors: Ambrose Cheung, Hanover, NH (US); Guido Memmi, White River Junction, VT (US)

(73) Assignee: TRUSTEES OF DARTMOUTH COLLEGE, Hanover, NH (US)

( * ) Notice: Subject to any disclaimer, the term of this patent is extended or adjusted under 35 U.S.C. 154(b) by 1825 days.

(21) Appl. No.: 12/670,457

(22) PCT Filed: Aug. 7, 2008

(86) PCT No.: PCT/US2008/072442
§ 371 (c)(1),
(2), (4) Date: Jan. 25, 2010

(87) PCT Pub. No.: WO2009/032470
PCT Pub. Date: Mar. 12, 2009

(65) Prior Publication Data
US 2010/0197649 A1    Aug. 5, 2010

Related U.S. Application Data

(60) Provisional application No. 60/957,314, filed on Aug. 22, 2007.

(51) Int. Cl.
| *A61K 31/545* | (2006.01) |
| *A61K 31/43* | (2006.01) |
| *A01N 37/18* | (2006.01) |
| *A61K 38/04* | (2006.01) |
| *A61K 45/06* | (2006.01) |
| *A61K 31/546* | (2006.01) |
| *C12Q 1/18* | (2006.01) |
| *C12Q 1/68* | (2006.01) |

(52) U.S. Cl.
CPC ............. *A61K 45/06* (2013.01); *A61K 31/546* (2013.01); *C12Q 1/18* (2013.01); *C12Q 1/689* (2013.01); *G01N 2333/31* (2013.01)

(58) Field of Classification Search
USPC ........................................................ 514/192
See application file for complete search history.

(56) References Cited

U.S. PATENT DOCUMENTS

| 2003/0216330 A1* | 11/2003 | Norden | A61K 31/42 514/29 |
| 2007/0060506 A1* | 3/2007 | Walsh | A61K 31/351 514/2.7 |
| 2009/0253129 A1* | 10/2009 | Goering et al. | 435/6 |

FOREIGN PATENT DOCUMENTS

| WO | WO 2007/058939 A2 | 5/2007 |
| WO | WO 2007058939 A2 * | 5/2007 |

OTHER PUBLICATIONS

Tentolouris et al., Methicillin-resistant *Staphylococcus aureus*: an increasing problem in a diabetic foot clinic, 1999, Diabetic Medicine, 16, pp. 767-771.*
Memmi et al., *Staphylococcus aureus* PBP4 Is Essential for beta-Lactam Resistance in Community-Acquired Methicillin-Resistant Strains, 2008, Antimicrobial Agents and Chemotherapy, vol. 52, No. 11, pp. 3955-3966.*
Arnaud et al. "New Vector for Efficient Allelic Replacement in Naturally Nontransformable, Low-GC-Content, Gram-Positive Bacteria" Applied and Environmental Microbiology 2004 vol. 70(6): 6887-6891.
Baba et al. "Genome and Virulence Determinants of High Virulence Community-Acquired MRSA" The Lancet 2002 vol. 359: 1819-1827.
Bratu et al. "A Population-Based Study Examining the Emergence of Community-Associated Methicillin-Resistant *Staphylococcus aureus* USA300 in New York City" Annals of Clinical Microbiology and Antimicrobials 2006 vol. 5: 29.
Cote et al. "Generation of Human Monoclonal Antibodies Reactive with Cellular Antigens" Proceedings of the National Academy of Science USA 1983 vol. 80: 2026-2030.
Fernandez et al. "Comparison of Efficacies of Oral Levofloxacin and Oral Ciprofloxacin in a Rabbit Model of a Staphylococcal Abscess" Antimicrobial Agents and Chemotherapy 1999 vol. 43(3): 667-671.
Finan et al. "Role of Penicillin-Binding Protein 4 in Expression of Vancomycin Resistance Among Clinical Isolates of Oxacillin-Resistant *Staphylococcus aureus*" Antimicrobial Agents and Chemotherapy 2001 vol. 45(11): 3070-3075.
Gales et al. "Emergence of Linezolid-Resistant *Staphylococcus aureus* During Treatment of Pulmonary Infection in a Patient with Cystic Fibrosis" International Journal of Antimicrobial Agents 2006 vol. 27: 300-302.
Gardete et al. "A Link in Transcription Between the Native *pbp*B and the Acquired *mec*A Gene in a Strain of *Staphylococcus aureus*" Microbiology 2006 vol. 152: 2549-2558.

(Continued)

*Primary Examiner* — Kortney L Klinkel
*Assistant Examiner* — Tori M Strong
(74) *Attorney, Agent, or Firm* — Licata & Tyrrell P.C.

(57) ABSTRACT

The present invention includes compositions and methods for diagnosing and treating CA-MRSA infections in patients. The methods are based on the finding that combining cefoxitin and a synthetic penicillin in a treatment regimen results in a synergistic effect of the two drugs, an effect that is related to PBP4 activity in CA-MRSA isolates. Also provided is a CA-MRSA-specific biomarker which can be used to detect the presence of a CA-MRSA infection in a patient.

3 Claims, 6 Drawing Sheets

(56) References Cited

OTHER PUBLICATIONS

Georgopapadakou, N.H. and Liu, F.Y. "Binding of Beta-Lactam Antibiotics to Penicillin-Binding Proteins of *Staphylococcus aureus* and *Streptococcus faecalis*: Relation to Antibacterial Activity" Antimicrobial Agents and Chemotherapy 1980 vol. 18(5): 834-836.

Georgopapadakou, N.H. and Liu F.Y. "Penicillin-Binding Proteins in Bacteria" Antimicrobial Agents and Chemotherapy 1980 vol. 18(1): 148-157.

Georgopapadakou et al. "Penicillin-Binding Proteins in a *Staphylococcus aureus* Strain Resistant to Specific Beta-Lactam Antibiotics" Antimicrobial Agents and Chemotherapy 1982 vol. 22(1): 172-175.

Gisby, J. and Bryant, J. "Efficacy of a New Cream Formulation of Mupirocin: Comparison with Oral and Topical Agents in Experimental Skin Infections" Antimicrobial Agents and Chemotherapy 2000 vol. 44(2): 255-260.

Godin et al. "A New Approach for Treatment of Deep Skin Infections by an Ethosomal Antibiotic Preparation: an In Vivo Study" Journal of Antimicrobial Chemotherapy 2005 vol. 55: 989-994.

Groom et al. "Community-Acquired Methicillin-Resistant *Staphylococcus aureus* in a Rural American Indian Community" JAMA 2001 vol. 286(10): 1201-1205.

Jung et al. "Antimicrobial Susceptibility and Clonal Relatedness Between Community- and Hospital-Acquired Methicillin-Resistant *Staphylococcus aureus* from Blood Cultures" the Journal of Microbiology 2006 vol. 44 (3) : 336-343.

Katayama et al. "Effect of Disruption of *Staphylococcus aureus* PBP4 Gene on Resistance to Beta-Lactam Antibiotics" Microbial Drug Resistance 2003 vol. 9(4): 329-336.

Kazakova et al. "A Clone of Methicillin-Resistant *Staphylococcus aureus* Among Professional Football Players" The New England Journal of Medicine 2005 vol. 352(5): 468-475.

Kernodle, D.S. and Kaiser, A.B. "Comparative Prophylactic Efficacies of Ciprofloxacin, Ofloxacin, Cefazolin, and Vancomycin in Experimental Model of Staphylococcal Wound Infection" Antimicrobial Agents and Chemotherapy 1994 vol. 38(6): 1325-1330.

King et al "Emergence of Community-Acquired Methicillin-Resistant *Staphylococcus aureus* USA 300 Clone as the Predominant Cause of Skin and Soft Tissue Infections" Annals of Internal Medicine 2006 vol. 144: 309-317.

Kohler et al. "Continuous Cultures of Fused Cells Secreting Antibody of Predefined Specificity" Nature 1975 vol. 256: 495-497.

Kourbatova et al. "Emergence of Community-Associated Methicillin-Resistant *Staphylococcus aureus* USA 300 Clone as a Cause of Health Care-Associated Infections Among Patients with Prosthetic Joint Infections" American Journal Infection Control 2005 vol. 33: 385-391.

Kozarich, J.W. and Strominger, J.L. "A Membrane Enzyme from *Staphylococcus aureus* Which Catalyzes Transpeptidase, Carboxypeptidase, and Penicillinase Activities" The Journal of Biological Chemistry 1978 vol. 253(4): 1272-1278.

Kozbor et al. "Specific Immunoglobulin Production and Enhanced Tumorigenicity Following Ascites Growth of Human Hybridomas" Journal of Immunological Methods 1985 vol. 81: 31-42.

Leski, T.A. and Thomasz, A. "Role of Penicillin-Binding Protein 2 (PBP2) in the Antibiotic Susceptibility and Cell Wall Cross-Linking of *Staphylococcus aureus*: Evidence for the Cooperative Functioning of PBP2, PBP4, PBP2A" Journal of Bacteriology 2005 vol. 187(5): 1815-1824.

Lina et al. "Involvement of Panton-Valentine Leukocidin-Producing *Staphylococcus aureus* in Primary Skin Infections and Pneumonia" Clinical Infectious Diseases 1999 vol. 29: 1128-1132.

Mallorqui-Fernadez et al. "Staphylococcal Methicillin Resistance: Fine Focus on Folds and Functions" FEMS Microbiology Letters 2004 vol. 235: 1-8.

Matsuda et al. "Autolysis of Methicillin-Resistant *Staphylococcus aureus* is Involved in Synergism Between Imipenem and Cefotiam" Antimicrobial Agents and Chemotherapy 1995 vol. 39(12): 2631-2634.

Matsuhashi et al. "Molecular Cloning of the Gene of a Penicillin-Binding Protein Supposed to Cause High Resistance to Beta-Lactam Antibiotics in *Staphylococcus aureus*" Journal of Bacteriology 1986 vol. 167(3): 975-980.

McKinney et al. "Transcription of the Gene Mediating Methicillin Resistance in *Staphylococcus aureus* (*mec*A) is Corepressed But Not Coinduced by Cognate *mec*A and Beta-Lactamase Regulators" Journal of Bacteriology 2001 vol. 183(23): 6862-6868.

Nair, S.R. and Cherubin, C.E. "Use of Cefoxitin, New Cephalosporin-Like Antibiotic, in the Treatment of Aerobic and Anaerobic Infections" Antimicrobial Agents and Chemotherapy 1978 vol. 14(6): 866-875.

O'Flaherty et al. "The Recombinant Phage Lysine LysK has a Broad Spectrum of Lytic Activity Against Clinically Relevant Staphylococci, Including Methicillin-Resistant *Staphylococcus aureus*" Journal of Bacteriology 2005 vol. 187(20): 7161-7164.

Patel et al. "Antistaphylococcal Activity of WCK 771, a Tricyclic Fluoroquinolone, in Animal Infection Models" Antimicrobial Agents and Chemotherapy 2004 vol. 48(12): 4754-4761.

Pinho et al. "Cloning, Characterization, and Inactivation of the Gene *pbp*C, Encoding Penicillin-Binding Protein 3 of *Staphylococcus Aureus*" Journal of Bacteriology 2000 vol. 182(4): 1074-1079.

Pinho et al. "An Acquired and a Native Penicillin-Binding Protein Cooperate in Building the Cell Wall of Drug Resistant Staphylococci" Proceedings of the National Academy of Science USA 2001 vol. 98(19): 10886-10891.

Schrader-Fischer, G. and Berger-Bächi, B. "The AbcA Transporter of *Staphylococcus aureus* Affects Cell Autolysis" Antimicrobial Agents and Chemotherapy 2001 vol. 45(2): 407-412.

Seybold et al "Emergence of Community-Associated Methicillin-Resistant *Staphylococcus aureus* USA300 Genotype as a Major Cause of Heath Care-Associated Blood Stream Infections" Clinical Infectious Diseases 2006 vol. 42: 647-656.

Sieradzki et al "Inactivated *pbp*4 in Highly Glycopeptide-Resistant Laboratory Mutants of *Staphylococcus aureus*" The Journal of Biological Chemistry 1999 vol. 274(27): 18942-18946.

Skiest, D.J. "Treatment Failure Resulting From Resistance of *Staphylococcus aureus* to Daptomycin" Journal of Clinical Microbiology 2006 vol. 44(2): 655-656.

Tomasz et al. "Stable Classes of Phenotypic Expression in Methicillin-Resistant Clinical Isolates of Staphylococci" Antimicrobial Agents and Chemotherapy 1991 vol. 35(1): 124-129.

Voyich et al. "Insights Into Mechanisms Used by *Staphylococcus aureus* to Avoid Destruction by Human Neutrophils" The Journal of Immunology 2005 vol. 175: 3907-3919.

\* cited by examiner

SEQUENCE LISTING

<160> NUMBER OF SEQ ID NOS: 26

<210> SEQ ID NO 1
<211> LENGTH: 1050
<212> TYPE: DNA
<213> ORGANISM: Staphylococcus aureus

<400> SEQUENCE: 1

```
ttgataccta cgctagaaga aattattgat aagtatggaa acttagttga ttatttgaaa      60
tttgatgtaa cagttgaggt ttatgaagat ttgttgttat taagaagttt aagcgattta     120
aatgaacatc aaaagatgga tagagtttca tttataaaaa aacatttaaa ctcaaatttc     180
gattatttat tagatgatac tgagtttaga agtatcaata agatttacag taatttaaat     240
atcatgacgc atatcaatag tcaaaataat aattttaaac gtaatccatt tataaatgaa     300
gaacaattga aatcactact cgcgataaag aaagtagatg cacatatgag ttatgattca     360
aatattactt caaaagcatt ggcagaaata aacaaaacgc aaaaaagatt agttacaaag     420
atagacacac tctataatca gtcaaaaaaa gaaaatgaat atgtacggtt aggagaaaaa     480
atatcgtata caaaattgga gaatcattgg aaatatttat ataatgagat tcagttttat     540
aatcttaata atcaattgat tagttatgtt gcattagaac aggaatatgc ttgggctttt     600
ttaaatgaac tattttattt gatagaattg tatttgaagg catttaaagg acaaaagaaa     660
acagattatg agtttgggaa aaaattaaac gaatttattc aatcatatgt cattatttta     720
cttatagata tacgattacc tgttgttaga ttatatatta ttagagacat tgtagataca     780
tgtgaaggag aaaaagataa ttacaaaaga attacactga tagaagaatc tattaaaaag     840
tatagatacg taaaagatca gattaaaaga tttaaaaatg gattagaaga atcgttatta     900
aatgcaactt tatctattga acaaaatatg ttgaaagtta aaattgatta ttataaagcc     960
tactgctttc ctagagaaaa aacaaagcat aacaatattg agtacaatgt atcgttgttt    1020
tttaaagcat tagatgcctt aaagaaatag                                      1050
```

<210> SEQ ID NO 2
<211> LENGTH: 349
<212> TYPE: PRT
<213> ORGANISM: Staphylococcus aureus

<400> SEQUENCE: 2

| Met | Ile | Pro | Thr | Leu | Glu | Glu | Ile | Ile | Asp | Lys | Tyr | Gly | Asn | Leu | Val |
|-----|-----|-----|-----|-----|-----|-----|-----|-----|-----|-----|-----|-----|-----|-----|-----|
| 1 | | | | 5 | | | | | 10 | | | | | 15 | |

| Asp | Tyr | Leu | Lys | Phe | Asp | Val | Thr | Val | Glu | Val | Tyr | Glu | Asp | Leu | Leu |
|-----|-----|-----|-----|-----|-----|-----|-----|-----|-----|-----|-----|-----|-----|-----|-----|
| | | | 20 | | | | | 25 | | | | | 30 | | |

| Leu | Leu | Arg | Ser | Leu | Ser | Asp | Leu | Asn | Glu | His | Gln | Lys | Met | Asp | Arg |
|-----|-----|-----|-----|-----|-----|-----|-----|-----|-----|-----|-----|-----|-----|-----|-----|
| | | | 35 | | | | | 40 | | | | | 45 | | |

| Val | Ser | Phe | Ile | Lys | Lys | His | Leu | Asn | Ser | Asn | Phe | Asp | Tyr | Leu | Leu |
|-----|-----|-----|-----|-----|-----|-----|-----|-----|-----|-----|-----|-----|-----|-----|-----|
| | 50 | | | | | 55 | | | | | 60 | | | | |

| Asp | Asp | Thr | Glu | Phe | Arg | Ser | Ile | Asn | Lys | Ile | Tyr | Ser | Asn | Leu | Asn |
|-----|-----|-----|-----|-----|-----|-----|-----|-----|-----|-----|-----|-----|-----|-----|-----|
| 65 | | | | | 70 | | | | | 75 | | | | | 80 |

| Ile | Met | Thr | His | Ile | Asn | Ser | Gln | Asn | Asn | Phe | Lys | Arg | Asn | Pro |
|-----|-----|-----|-----|-----|-----|-----|-----|-----|-----|-----|-----|-----|-----|-----|
| | | | | 85 | | | | | 90 | | | | | 95 |

| Phe | Ile | Asn | Glu | Glu | Gln | Leu | Lys | Ser | Leu | Leu | Ala | Ile | Lys | Lys | Val |
|-----|-----|-----|-----|-----|-----|-----|-----|-----|-----|-----|-----|-----|-----|-----|-----|
| | | | 100 | | | | | 105 | | | | | 110 | | |

| Asp | Ala | His | Met | Ser | Tyr | Asp | Ser | Asn | Ile | Thr | Ser | Lys | Ala | Leu | Ala |
|-----|-----|-----|-----|-----|-----|-----|-----|-----|-----|-----|-----|-----|-----|-----|-----|
| | | | 115 | | | | | 120 | | | | | 125 | | |

| Glu | Ile | Asn | Lys | Thr | Gln | Lys | Arg | Leu | Val | Thr | Lys | Ile | Asp | Thr | Leu |
|-----|-----|-----|-----|-----|-----|-----|-----|-----|-----|-----|-----|-----|-----|-----|-----|
| | | | 130 | | | | | 135 | | | | | 140 | | |

| Tyr | Asn | Gln | Ser | Lys | Lys | Glu | Asn | Glu | Tyr | Val | Arg | Leu | Gly | Glu | Lys |
|-----|-----|-----|-----|-----|-----|-----|-----|-----|-----|-----|-----|-----|-----|-----|-----|
| 145 | | | | | 150 | | | | | 155 | | | | | 160 |

| Ile | Ser | Tyr | Thr | Lys | Leu | Glu | Asn | His | Trp | Lys | Tyr | Leu | Tyr | Asn | Glu |
|-----|-----|-----|-----|-----|-----|-----|-----|-----|-----|-----|-----|-----|-----|-----|-----|
| | | | | 165 | | | | | 170 | | | | | 175 | |

| Ile | Gln | Phe | Tyr | Asn | Leu | Asn | Asn | Gln | Leu | Ile | Ser | Tyr | Val | Ala | Leu |
|-----|-----|-----|-----|-----|-----|-----|-----|-----|-----|-----|-----|-----|-----|-----|-----|
| | | | 180 | | | | | 185 | | | | | 190 | | |

| Glu | Gln | Glu | Tyr | Ala | Trp | Ala | Phe | Leu | Asn | Glu | Leu | Phe | Tyr | Leu | Ile |
|-----|-----|-----|-----|-----|-----|-----|-----|-----|-----|-----|-----|-----|-----|-----|-----|
| | | | 195 | | | | | 200 | | | | | 205 | | |

| Glu | Leu | Tyr | Leu | Lys | Ala | Phe | Lys | Gly | Gln | Lys | Lys | Thr | Asp | Tyr | Glu |
|-----|-----|-----|-----|-----|-----|-----|-----|-----|-----|-----|-----|-----|-----|-----|-----|
| | 210 | | | | | 215 | | | | | 220 | | | | |

| Phe | Gly | Lys | Lys | Leu | Asn | Glu | Phe | Ile | Gln | Ser | Tyr | Val | Ile | Ile | Leu |
|-----|-----|-----|-----|-----|-----|-----|-----|-----|-----|-----|-----|-----|-----|-----|-----|
| 225 | | | | | 230 | | | | | 235 | | | | | 240 |

| Leu | Ile | Asp | Ile | Arg | Leu | Pro | Val | Val | Arg | Leu | Tyr | Ile | Ile | Arg | Asp |
|-----|-----|-----|-----|-----|-----|-----|-----|-----|-----|-----|-----|-----|-----|-----|-----|
| | | | | 245 | | | | | 250 | | | | | 255 | |

| Ile | Val | Asp | Thr | Cys | Glu | Gly | Glu | Lys | Asp | Asn | Tyr | Lys | Arg | Ile | Thr |
|-----|-----|-----|-----|-----|-----|-----|-----|-----|-----|-----|-----|-----|-----|-----|-----|
| | | | 260 | | | | | 265 | | | | | 270 | | |

| Leu | Ile | Glu | Glu | Ser | Ile | Lys | Lys | Tyr | Arg | Tyr | Val | Lys | Asp | Gln | Ile |
|-----|-----|-----|-----|-----|-----|-----|-----|-----|-----|-----|-----|-----|-----|-----|-----|
| | 275 | | | | | 280 | | | | | 285 | | | | |

| Lys | Arg | Phe | Lys | Asn | Gly | Leu | Glu | Ser | Leu | Leu | Asn | Ala | Thr | Leu |
|-----|-----|-----|-----|-----|-----|-----|-----|-----|-----|-----|-----|-----|-----|-----|
| | 290 | | | | | 295 | | | | | 300 | | | |

| Ser | Ile | Glu | Gln | Asn | Met | Leu | Lys | Val | Lys | Ile | Asp | Tyr | Tyr | Lys | Ala |
|-----|-----|-----|-----|-----|-----|-----|-----|-----|-----|-----|-----|-----|-----|-----|-----|
| 305 | | | | | 310 | | | | | 315 | | | | | 320 |

| Tyr | Cys | Phe | Pro | Arg | Glu | Lys | Thr | Lys | His | Asn | Asn | Ile | Glu | Tyr | Asn |
|-----|-----|-----|-----|-----|-----|-----|-----|-----|-----|-----|-----|-----|-----|-----|-----|
| | | | | 325 | | | | | 330 | | | | | 335 | |

| Val | Ser | Leu | Phe | Phe | Lys | Ala | Leu | Asp | Ala | Leu | Lys | Lys |
|-----|-----|-----|-----|-----|-----|-----|-----|-----|-----|-----|-----|-----|
| | | | 340 | | | | | 345 | | | | |

<210> SEQ ID NO 3
<211> LENGTH: 1491
<212> TYPE: DNA
<213> ORGANISM: Staphylococcus aureus

<400> SEQUENCE: 3

```
ttgcatagag aaagtaaata tatagagtat aagaaatcac gaaaaggatt atctaatgat      60
atttggtcta cgtatagtgc ttttgcaaat actgaaggtg gtactatata ttaggaatt     120 gaagaaaaaa agatcgagga caaaaagtc tttgtttcag ttggtgttga agatccagag     180
```

```
aaaatgattg aagatttttg gaatgcacta tatggaagaa gtaaagttag tcaaaatatt    240
ttatcaaata aagatgttaa aattgttaat attgaaaata aagcgtgcat tgaaattcat    300
gtaccagaag cgccttattc gaagaaaccg atatatgtag ataataaaaa agatttagta    360
tataaaagag ttgatgatgc tgatagaatt gcgactgaag aagagtataa attcatgatt    420
gtaaattctc aagacgatat agatacagaa ttattagata actatgacat gtctgattta    480
aatcacgaat ctatcgaaaa ttataggaaa cttctattaa aaaatactaa tgatgagaga    540
tatgcgaata tgagccaact ggatttaatg atagatttag gagcatatag aaaagataga    600
agttcgaaag acaaacagta taaaatgact acagcatgtt tattattctt tggtaagtat    660
aatgcgatta gtgatagatt cccaggattt caattagatt attttaagaa aacaaattac    720
ctagatactg attggaaaga tagaaatatca agtggagatt taggtaatga agatttaaac    780
gtgtatagtt tttttgaaaa agtattgata aaattaactg ataacattga ggaatcattt    840
agcctaaatg atggtttgac tagacaaaat tatgcaagag atttaaaagt agcaattcgc    900
gaagcactgg ttaatacatt aatgcatgcg tattatgata ctaagcaaag tattaaaata    960
gttaattgtg aagattttat agagttttat aatccgggta tatgagaat aaataaagaa    1020 gattttattc atggagggca ttcaaaggac agaaatagta tattatcgac gcttttcaga    1080
agagtaggat attcagaaaa agctggatct ggaggaccaa ggatattcga tgtagttaat    1140
agacataagc ttaaaacgcc tgaaatagaa ttaacggaca tggacactaa tgtagtactt    1200
tggaaacaag atttaatgaa ggagtttgaa aaatatcctg agttagacaa aaagtaata    1260 aagtatatta ttgactatgg atcaataagt aagggtgaag ccttaaaaat ggaaaatatg    1320
acagaatatc agtttagaaa tatttaaaaa aactaaaag atgataactt gataaaaaaa    1380
gaaggtgaag gtccggctac taaatatgtg ttaatagaat caaagaagc tgatatattg    1440 cgaactaaaa aagtaattaa aagtttagag tctttctta ggaataaata a              1491
```

<210> SEQ ID NO 4
<211> LENGTH: 496
<212> TYPE: PRT
<213> ORGANISM: Staphylococcus aureus

<400> SEQUENCE: 4

```
Met His Arg Glu Ser Lys Tyr Ile Glu Tyr Lys Ser Arg Lys Gly
1               5                   10                  15

Leu Ser Asn Asp Ile Trp Ser Thr Tyr Ser Ala Phe Ala Asn Thr Glu
                20                  25                  30

Gly Gly Thr Ile Tyr Leu Gly Ile Glu Glu Lys Lys Ile Glu Asp Lys
            35                  40                  45

Lys Val Phe Val Ser Val Gly Val Glu Asp Pro Glu Lys Met Ile Glu
        50                  55                  60

Asp Phe Trp Asn Ala Leu Tyr Gly Arg Ser Lys Val Ser Gln Asn Ile
65                  70                  75                  80

Leu Ser Asn Lys Asp Val Lys Ile Val Asn Ile Glu Asn Lys Ala Cys
                85                  90                  95

Ile Glu Ile His Val Pro Glu Ala Pro Tyr Ser Lys Lys Pro Ile Tyr
            100                 105                 110

Val Asp Asn Lys Lys Asp Leu Val Tyr Lys Arg Val Asp Asp Ala Asp
        115                 120                 125

Arg Ile Ala Thr Glu Glu Glu Tyr Lys Phe Met Ile Val Asn Ser Gln
    130                 135                 140
```

Asp Asp Ile Asp Thr Glu Leu Leu Asp Asn Tyr Asp Met Ser Asp Leu
145                 150                 155                 160

Asn His Glu Ser Ile Glu Asn Tyr Arg Lys Leu Leu Leu Lys Asn Thr
            165                 170                 175

Asn Asp Glu Arg Tyr Ala Asn Met Ser Gln Leu Asp Leu Met Ile Asp
        180                 185                 190

Leu Gly Ala Tyr Arg Lys Asp Arg Ser Ser Lys Asp Lys Gln Tyr Lys
    195                 200                 205

Met Thr Thr Ala Cys Leu Leu Phe Phe Gly Lys Tyr Asn Ala Ile Ser
210                 215                 220

Asp Arg Phe Pro Gly Phe Gln Leu Asp Tyr Phe Lys Lys Thr Asn Tyr
225                 230                 235                 240

Leu Asp Thr Asp Trp Lys Asp Arg Ile Ser Ser Gly Asp Leu Gly Asn
                245                 250                 255

Glu Asp Leu Asn Val Tyr Ser Phe Phe Glu Lys Val Leu Ile Lys Leu
            260                 265                 270

Thr Asp Asn Ile Glu Glu Ser Phe Ser Leu Asn Asp Gly Leu Thr Arg
        275                 280                 285

Gln Asn Tyr Ala Arg Asp Leu Lys Val Ala Ile Arg Glu Ala Leu Val
    290                 295                 300

Asn Thr Leu Met His Ala Tyr Tyr Asp Thr Lys Gln Ser Ile Lys Ile
305                 310                 315                 320

Val Asn Cys Glu Asp Phe Ile Glu Phe Tyr Asn Pro Gly Asn Met Arg
                325                 330                 335

Ile Asn Lys Glu Asp Phe Ile His Gly Gly His Ser Lys Asp Arg Asn
            340                 345                 350

Ser Ile Leu Ser Thr Leu Phe Arg Arg Val Gly Tyr Ser Glu Lys Ala
        355                 360                 365

Gly Ser Gly Gly Pro Arg Ile Phe Asp Val Val Asn Arg His Lys Leu
    370                 375                 380

Lys Thr Pro Glu Ile Glu Leu Thr Asp Met Asp Thr Asn Val Val Leu
385                 390                 395                 400

Trp Lys Gln Asp Leu Met Lys Glu Phe Glu Lys Tyr Pro Glu Leu Asp
                405                 410                 415

Lys Lys Val Ile Lys Tyr Ile Ile Asp Tyr Gly Ser Ile Ser Lys Gly
            420                 425                 430

Glu Ala Leu Lys Met Glu Asn Met Thr Glu Tyr Gln Phe Arg Asn Ile
        435                 440                 445

Leu Lys Lys Leu Lys Asp Asp Asn Leu Ile Lys Lys Glu Gly Glu Gly
    450                 455                 460

Pro Ala Thr Lys Tyr Val Leu Ile Glu Ser Lys Glu Ala Asp Ile Leu
465                 470                 475                 480

Arg Thr Lys Lys Val Ile Lys Ser Leu Glu Ser Phe Phe Arg Asn Lys
                485                 490                 495

<210> SEQ ID NO 5
<211> LENGTH: 372
<212> TYPE: DNA
<213> ORGANISM: Staphylococcus aureus

<400> SEQUENCE: 5
ttgaaaacga atattttaaa tttagataat gagttagaaa acactgaata tgtcgaaggt      60
aaaccatatg tacagtacgg tattaaatat gaaagaaatc aggcattaag aaatgaagct     120

```
attaaaattc atggaactac atgtaaagta tgtggatttg attttaaagc taagtatggc    180
gatttaggtg agggttttat tgaaattcat catttaaaac caatgttttc aataaaaaga    240
gaaataaaag taaatccaca aaaagattta gtcccactat gttctaattg ccataaaatg    300
attcatagaa atactaaaaa acctttaacg attaaagaat taaccaaaat agttaattat    360
aatagcaaat aa                                                        372
```

<210> SEQ ID NO 6
<211> LENGTH: 206
<212> TYPE: PRT
<213> ORGANISM: Staphylococcus aureus

<400> SEQUENCE: 6

```
Met Lys Phe Thr Glu Val Glu Val Ile Glu His Leu Val Lys Ala Tyr
1               5                   10                  15

Lys Glu Ala Gly Lys Pro Thr Tyr Pro His Glu Asn Leu Tyr Arg Gly
                20                  25                  30

Arg Asn His Ser Ile Ser Gly Ile Gly Glu Asp Leu Leu Gly Ala Tyr
            35                  40                  45

Leu Ile Ser Arg Leu Glu Gly Val Gln Ile Phe Ile Asp Gln Pro Leu
        50                  55                  60

Ser Met Ile Asp Lys Ser Leu Ser Thr Arg Tyr Pro Asp Leu Leu Ile
65                  70                  75                  80

Cys Glu Asp Asn Glu Ile Lys Asn Ile Leu Glu Val Lys Met Asp Leu
                85                  90                  95

Gly Tyr Gln Arg Lys Asp Phe Ile Asp Tyr Cys Arg Lys Lys Glu Glu
            100                 105                 110

Trp Ile Ser Asn Ile Val Gly Lys Gln Cys Val Leu Ser Arg Lys Arg
        115                 120                 125

Glu Asp Lys Ile Pro Met Asn Ile Ala Asp Asp Ile Lys Phe His Val
    130                 135                 140

Val Ile Tyr Ser Glu Asn Asn Gly Pro Lys Arg Phe Asp Glu Glu Ile
145                 150                 155                 160

Met Pro Ile Val Asn Glu Thr Cys Pro His Ile Glu Val Tyr Val Leu
                165                 170                 175

Thr Ser Gly Gln His Pro Asn Leu Val Asn Val Asn Leu Glu Gly Ile
            180                 185                 190

Asn Ile Asn Lys Asp Glu Phe Glu Ile Leu Val Asn Ala Leu
        195                 200                 205
```

<210> SEQ ID NO 7
<211> LENGTH: 621
<212> TYPE: DNA
<213> ORGANISM: Staphylococcus aureus

<400> SEQUENCE: 7

```
atgaaattca ctgaagtgga agttatcgaa catcttgtaa aggcatataa agaagcagga     60
aagcctactt atcctcatga aaatttatat cgaggacgta atcatagtat ttcaggtatt    120
ggagaagact tgctgggtgc ttatttgatt agtagattgg aaggtgtcca aatatttatt    180
gatcagcctt tatctatgat tgataaatct ttaagtacaa gatatccgga tttattaatt    240
tgtgaagata tgaaattaa aaatatacta gaagttaaaa tggacttagg atatcaaaga    300
aaagatttta gagattattg ccgaaagaaa gaagaatgga tttcaaatat cgtaggaaaa    360
cagtgtgtat tgtctagaaa gagagaagac aaaattccta tgaatatagc tgatgatatt    420
```

```
aaatttcatg ttgtgattta cagtgaaaac aatggaccga agcggtttga tgaagaaatc    480
atgcctatcg ttaatgaaac atgtccacat attgaagtat atgtcctaac aagcggtcaa    540
caccctaatt tagtaaatgt taatcttgaa ggtattaata ttaataaaga tgaatttgaa    600
atattagtaa atgcgttata a                                              621

<210> SEQ ID NO 8
<211> LENGTH: 206
<212> TYPE: PRT
<213> ORGANISM: Staphylococcus aureus

<400> SEQUENCE: 8

Met Lys Phe Thr Glu Val Glu Val Ile Glu His Leu Val Lys Ala Tyr
1               5                   10                  15

Lys Glu Ala Gly Lys Pro Thr Tyr Pro His Glu Asn Leu Tyr Arg Gly
            20                  25                  30

Arg Asn His Ser Ile Ser Gly Ile Gly Glu Asp Leu Leu Gly Ala Tyr
        35                  40                  45

Leu Ile Ser Arg Leu Glu Gly Val Gln Ile Phe Ile Asp Gln Pro Leu
    50                  55                  60

Ser Met Ile Asp Lys Ser Leu Ser Thr Arg Tyr Pro Asp Leu Leu Ile
65                  70                  75                  80

Cys Glu Asp Asn Glu Ile Lys Asn Ile Leu Glu Val Lys Met Asp Leu
                85                  90                  95

Gly Tyr Gln Arg Lys Asp Phe Ile Asp Tyr Cys Arg Lys Lys Glu Glu
            100                 105                 110

Trp Ile Ser Asn Ile Val Gly Lys Gln Cys Val Leu Ser Arg Lys Arg
        115                 120                 125

Glu Asp Lys Ile Pro Met Asn Ile Ala Asp Asp Ile Lys Phe His Val
    130                 135                 140

Val Ile Tyr Ser Glu Asn Asn Gly Pro Lys Arg Phe Asp Glu Glu Ile
145                 150                 155                 160

Met Pro Ile Val Asn Glu Thr Cys Pro His Ile Glu Val Tyr Val Leu
                165                 170                 175

Thr Ser Gly Gln His Pro Asn Leu Val Asn Val Asn Leu Glu Gly Ile
            180                 185                 190

Asn Ile Asn Lys Asp Glu Phe Glu Ile Leu Val Asn Ala Leu
        195                 200                 205

<210> SEQ ID NO 9
<211> LENGTH: 1092
<212> TYPE: DNA
<213> ORGANISM: Staphylococcus aureus

<400> SEQUENCE: 9
atgattagac gcggaacaaa aaatggggag gggggtata tattgatacc tacgctagaa    60
gaaattattg ataagtatgg aaacttagtt gattatttga aatttgatgt aacagttgag    120
gtttatgaag atttgttgtt attaagaagt ttaagcgatt taaatgaaca tcaaaagatg    180
gatagagttt catttataaa aaaacattta aactcaaatt tcgattattt attagatgat    240
actgagttta gaagtatcaa taagatttac agtaatttaa atatcatgac gcatatcaat    300
agtcaaaata taatttttaa acgtaatcca tttataaatg aagaacaatt gaaatcacta    360
ctcgcgataa agaagtagaa tgcacatatg agttatgatt caaatattac ttcaaaagca    420
ttggcagaaa taaacaaaac gcaaaaaaga ttagttacaa agatagacac actctataat    480
```

-continued

```
cagtcaaaaa aagaaaatga atatgtacgg ttaggagaaa aaatatcgta tacaaaattg    540
gagaatcatt ggaaatattt atataatgag attcagtttt ataatcttaa taatcaattg    600
attagttatg ttgcattaga acaggaatat gcttgggctt ttttaaatga actatttat    660 ttgatagaat tgtatttgaa ggcatttaaa ggacaaaaga aaacagatta tgagtttggg    720
aaaaaattaa acgaatttat tcaatcatat gtcattattt tacttataga tatacgatta    780
cctgttgtta gattatatat tattagagac attgtagata catgtgaagg agaaaaagat    840
aattacaaaa gaattacact gatagaagaa tctattaaaa agtatagata cgtaaaagat    900
cagattaaaa gatttaaaaa tggattaaaa gaatcgttat aaatgcaac tttatctatt     960 gaacaaaata tgttgaaagt taaaattgat tattataaag cctactgctt tcctagagaa   1020
aaaacaaagc ataacaatat tgagtacaat gtatcgttgt tttttaaagc attagatgcc   1080
ttaaagaaat ag                                                        1092
```

<210> SEQ ID NO 10
<211> LENGTH: 363
<212> TYPE: PRT
<213> ORGANISM: Staphylococcus aureus

<400> SEQUENCE: 10

```
Met Ile Arg Arg Gly Thr Lys Asn Gly Glu Gly Gly Tyr Ile Leu Ile
1               5                   10                  15

Pro Thr Leu Glu Glu Ile Ile Asp Lys Tyr Gly Asn Leu Val Asp Tyr
            20                  25                  30

Leu Lys Phe Asp Val Thr Val Glu Val Tyr Glu Asp Leu Leu Leu Leu
        35                  40                  45

Arg Ser Leu Ser Asp Leu Asn Glu His Gln Lys Met Asp Arg Val Ser
    50                  55                  60

Phe Ile Lys Lys His Leu Asn Ser Asn Phe Asp Tyr Leu Leu Asp Asp
65                  70                  75                  80

Thr Glu Phe Arg Ser Ile Asn Lys Ile Tyr Ser Asn Leu Asn Ile Met
                85                  90                  95

Thr His Ile Asn Ser Gln Asn Asn Asn Phe Lys Arg Asn Pro Phe Ile
            100                 105                 110

Asn Glu Glu Gln Leu Lys Ser Leu Leu Ala Ile Lys Lys Val Asp Ala
        115                 120                 125

His Met Ser Tyr Asp Ser Asn Ile Thr Ser Lys Ala Leu Ala Glu Ile
    130                 135                 140

Asn Lys Thr Gln Lys Arg Leu Val Thr Lys Ile Asp Thr Leu Tyr Asn
145                 150                 155                 160

Gln Ser Lys Lys Glu Asn Glu Tyr Val Arg Leu Gly Glu Lys Ile Ser
                165                 170                 175

Tyr Thr Lys Leu Glu Asn His Trp Lys Tyr Leu Tyr Asn Glu Ile Gln
            180                 185                 190

Phe Tyr Asn Leu Asn Asn Gln Leu Ile Ser Tyr Val Ala Leu Glu Gln
        195                 200                 205

Glu Tyr Ala Trp Ala Phe Leu Asn Glu Leu Phe Tyr Leu Ile Glu Leu
    210                 215                 220

Tyr Leu Lys Ala Phe Lys Gly Gln Lys Lys Thr Asp Tyr Glu Phe Gly
225                 230                 235                 240

Lys Lys Leu Asn Glu Phe Ile Gln Ser Tyr Val Ile Ile Leu Leu Ile
                245                 250                 255

Asp Ile Arg Leu Pro Val Val Arg Leu Tyr Ile Ile Arg Asp Ile Val
```

```
                  260                 265                 270
Asp Thr Cys Glu Gly Glu Lys Asp Asn Tyr Lys Arg Ile Thr Leu Ile
            275                 280                 285

Glu Glu Ser Ile Lys Lys Tyr Arg Tyr Val Lys Asp Gln Ile Lys Arg
            290                 295                 300

Phe Lys Asn Gly Leu Glu Glu Ser Leu Leu Asn Ala Thr Leu Ser Ile
305                 310                 315                 320

Glu Gln Asn Met Leu Lys Val Lys Ile Asp Tyr Tyr Lys Ala Tyr Cys
                325                 330                 335

Phe Pro Arg Glu Lys Thr Lys His Asn Asn Ile Glu Tyr Asn Val Ser
            340                 345                 350

Leu Phe Phe Lys Ala Leu Asp Ala Leu Lys Lys
            355                 360

<210> SEQ ID NO 11
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 11
tgatgtaaca gttgaggttt atgaagatt                                    29

<210> SEQ ID NO 12
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 12
ctttgtaact aatcttttt gcgttttg                                      28

<210> SEQ ID NO 13
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 13
gcgtgcattg aaattcatgt acc                                          23

<210> SEQ ID NO 14
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 14
ccaaagaata ataaacatgc tgtagtca                                     28

<210> SEQ ID NO 15
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 15
gaaagaaatc aggcattaag aaatgaag                                     28
```

<210> SEQ ID NO 16
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 16
ttatttgcta ttataattaa ctattttggt                              30

<210> SEQ ID NO 17
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 17
caggtattgg agaagacttg ctgg                                    24

<210> SEQ ID NO 18
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 18
attaacgata ggcatgattt cttcatc                                 27

<210> SEQ ID NO 19
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 19
ggtactgcta tccaccctca aa                                      22

<210> SEQ ID NO 20
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 20
ttacgacttg ttgcatacca tca                                     23

<210> SEQ ID NO 21
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 21
attggcagaa ataaacaaaa cg                                      22

<210> SEQ ID NO 22
<211> LENGTH: 23
<212> TYPE: DNA
<213> ORGANISM: Artificial sequence
<220> FEATURE:

```
<223> OTHER INFORMATION: Synthetic oligonucleotide

<400> SEQUENCE: 22
tcgtttaatt ttttcccaaa ctc                                              23

<210> SEQ ID NO 23
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 23
gtttcagttg gtgttgaaga tcc                                              23

<210> SEQ ID NO 24
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 24
cctataattt tcgatagatt cgtg                                             24

<210> SEQ ID NO 25
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 25
aggcatataa agaagcagga aag                                              23

<210> SEQ ID NO 26
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 26
cacactgttt tcctacgata tttg                                             24
```

COMPOSITIONS AND METHODS FOR DIAGNOSING AND TREATING COMMUNITY-ACQUIRED METHICILLIN-RESISTANT *STAPHYLOCOCCUS AUREUS*

This patent application is the National Stage of International Application No. PCT/US2008/072442 filed Aug. 7, 2008, which claims the benefit of priority from U.S. Provisional Ser. No. 60/957,314 filed Aug. 22, 2007, teachings of each of which are herein incorporated by reference in their entirety.

BACKGROUND OF THE INVENTION

Methicillin-resistant *Staphylococcus aureus* (MRSA) infections are the most common cause of nosocomial or hospital-acquired infections (Archer, G. L. 1998. *Clin. Infect. Dis.* 26:1179). However, the incidence of MRSA infections has substantially increased over the last five years in healthy individuals without any known risk factors due to the worldwide emergence of distinct MRSA strains known collectively as community acquired methicillin resistant *S. aureus* (CA-MRSA) (e.g., Groom, A. V. et al. 2001. *JAMA* 286:1201-1205; Kazakova, S. V. et al. 2005. *N. Engl. J. Med.* 352:468-475; King, M. D. et al. 2006. *Ann. Intern. Med.* 144:309-317; Bratu, S. et al. 2006. *Ann. Clin. Microbiol. Antimicrob.* 5:29). CA-MRSA strains have become the most frequent cause of skin and soft tissue infections in emergency rooms in the U.S., increasing in proportion from 29% in 2001-2002 to 64% in 2003-2004 (King, M. D. et al. 2006. *Ann. Intern. Med.* 144:309-317; Moran, G. J. et al. 2005. *Emerg. Infect. Dis.* 11:928-930; Moran, G. J. et al. 2006. *NEJM* 355:666-674). CA-MRSA strains appear to have evolved independently of hospital-acquired MRSA (HA-MRSA) and are genetically distinct from HA-MRSA. Moreover, many strains of CA-MRSA are more virulent than HA-MRSA, causing a different spectrum of symptoms and effects, which include necrotizing fasciitis and pneumonia in otherwise healthy individuals, but also carrying with it a different antibiotic resistance profile. CA-MRSA is now the most common cause of skin infections in the United States. The epidemiological characteristics of CA-MRSA and HA-MRSA are therefore distinct from each other and CA-MRSA requires attention as an independent and increasingly important public health problem.

USA300 and MW2 (USA400), representing two distinct isolates by pulsed-field electrophoresis, are the predominant strains of CA-MRSA in the U.S. (Groom, A. V. et al. 2001. *JAMA* 286:1201-1205; Baba, T. et al. 2002. *Lancet* 359: 1819-1827). Although initially seen in cutaneous infections, USA300, for example, has now become a major cause of sepsis and prosthetic joint infections with limited therapeutic options (Seybold, U. et al. 2006. *Clin. Infect. Dis.* 42:647-656; Kourbatova, E. V. et al. 2005. *Am. J. Infect. Control* 33:385-391; Gales, A. C. et al. 2006. *Int. J. Antimicrob. Agents* 27:300; Skiest, D. J. 2006. *J. Clin. Microbiol.* 44:655-656). Although HA-MRSA and CA-MRSA *S. aureus* strains have a similar core genome, they do carry substantial genetic and phenotypic differences which may explain why CA-MRSA strains are significantly more virulent in a mouse model of *S. aureus* infection, with a greater level of pathology in major vital organs, more resistant to killing by human PMNs and capable of causing greater host cell lysis (Voyich, J. M. et al. 2005. *J. Immunol.* 175:3907-3919). Thus, there is a need to understand and define the basis for CA-MRSA apart from HA-MRSA, including the potential treatments that may be unique for each type of MRSA. There is currently no reliable method to quickly and accurately diagnose CA-MRSA, distinguishing it from HA-MRSA, as well as a diminishing number of options for treatment of CA-MRSA infections.

Resistance to a greater number of antibiotics has occurred in *S. aureus* isolates worldwide. Besides common resistance to methicillin and β-lactams in general, *S. aureus* has also become resistant to drugs of last resort such as vancomycin, linezolid and daptomycin (Gales, A. C. et al. 2006. *Int. J. Antimicrob. Agents* 27:300-302; Skiest, D. J. 2006. *J. Clin. Microbiol.* 44:655-656; Howden, B. P. et al. 2004. *Clin. Infect. Dis.* 39:1544; Ruiz, M. E. et al. 2002. *Clin. Infect. Dis.* 35:1018-1020; Saner, F. H. et al. 2006. *Liver Transpl.* 12:1689-1692; Hirschwerk, D. et al. 2006. *Infect. Control Hosp. Epidemiol.* 27:315-317). All *S. aureus* isolates, both methicillin sensitive and resistant strains, carry three high molecular weight penicillin binding proteins, PBP1, PBP2 and PBP3 to which most β-lactam antibiotics bind, and a low molecular weight PBP called PBP4 which binds poorly to most β-lactams. PBP1 and PBP2 are essential enzymes involved in the synthesis of bacterial cell wall; the β-lactam antibiotics generally kill bacteria by interfering with the transpeptidase domain of penicillin binding proteins (PBPs), which leads to a loss of cell-wall cross-linking and integrity (Mallorqui-Fernandez, G. et al. 2004. *FEMS Microbiol. Lett.* 235:1-8). PBP4, the single low molecular weight PBP, has been shown to have a low affinity for most β-lactams, and is unique among low-molecular weight PBPs found among prokaryotes in that it possesses transpeptidase and carboxypeptidase activities (Kozarich, J. W. and J. L. Strominger. 1978. *J. Biol. Chem.* 253:1272-1278; Georgopapadakou, N. H. and F. Y. Liu. 1980. *Antimicrob. Agents Chemother.* 18:834-836; Georgopapadakou, N. H. and F. Y. Liu. 1980. *Antimicrob. Agents Chemother.* 18:148-157; Georgopapadakou, N. H. et al. 1982. *Antimicrob. Agents Chemother.* 22:172-175).

Methicillin resistance is achieved by acquisition of another high molecular weight PBP, namely PBP2A encoded by mecA; this is situated in the chromosome in a genomic island designated staphylococcal cassette chromosome mec (SCCmec). Unlike innate penicillin binding proteins, PBP2A has a remarkably low affinity for all β-lactams (Matsuhashi, M. et al. 1986. *J. Bacteriol.* 167:975).

In one study, PBP4 was shown to play a role in the synergistic effect of combining imipenem, an autolytic agent, with cefotiam, a compound with no affinity for PBP4, against MRSA; the synergistic activity of the two agents against MRSA was correlated with the degree of autolysis induced by imipenem (Matsuda, K. et al. 1995. *Antimicrob. Agents Chemother.* 39:2631-2634). PBP4 expression levels have been shown to affect vancomycin susceptibility in *S. aureus* strains COL, RN450M and N315 (Finan, J. E. et al. 2001. *Antimicrob. Agents Chemother.* 45:3070-3075). Previous studies also have linked loss of PBP4 to a drastic reduction in peptidoglycan cross-linking in MSSA, MRSA COL and also glycopeptide-resistant *S. aureus* (Sieradzki, K. et al. 1999. *J. Biol. Chem.* 274:18942-18946). However, in a recent study, a deletion of the PBP4 gene in the HA-MRSA prototypic strain COL was not lethal and had relatively little effect on β-lactam resistance (Katayama, Y. et al. 2003. *Microb. Drug Resist.* 9:329-336); the authors, therefore, concluded that PBP4 is a relatively unimportant target for β-lactam antibiotics in MRSA as well as methicillin-susceptible *S. aureus*.

As a consequence of the differences in epidemiology, virulence, and antibiotic susceptibility, there remains a need to be able to distinguish quickly and accurately between CA-MRSA and HA-MRSA infections. Without such distinction, patients are at risk of being improperly or tardily diagnosed, and/or receiving ineffective treatments and developing more severe infection, situations which can result in dire consequences for the patient, including death

SUMMARY OF THE INVENTION

The present invention features a composition for identifying CA-MRSA. This composition comprises an agent that binds a CA-MRSA-specific biomarker gene or gene product. In particular embodiments, the agent is used in a method of diagnosing a CA-MRSA infection by contacting a test sample from a human subject with the agent and detecting the presence or absence of binding of the test agent to a CA-MRSA-specific biomarker gene or gene product, wherein the presence of binding is indicative of a CA-MRSA infection. In particular embodiments, the agent binds the CA-MRSA-specific biomarker gene or gene product MW0042, MW0043, MW0046, MW0047, USA300_0041, USA300_0042, USA300_0042, USA300_0045, or USA300_0046.

Yet another object of the present invention is a method of diagnosing a CA-MRSA infection in a patient which comprises contacting a strain of MW2 and USA300 in vitro with cefoxitin and oxacillin to determine a first minimum inhibitory concentration level for oxacillin in the presence of a less than minimum inhibitory concentration level of cefoxitin against; contacting blood, organ or tissue isolates from a patient suspected of having a CA-MRSA infection in vitro with cefoxitin and oxacillin to determine a second minimum inhibitory concentration level for oxacillin in the presence of a less than minimum inhibitory concentration level of cefoxitin; comparing the first minimum inhibitory concentration level with the second minimum inhibitory concentration. In one embodiment, the minimum inhibitory concentration levels of cefoxitin and oxacillin against MW2 and USA300 are equal to or less than 2 microgram per milliliter.

Yet another object of the present invention is a method for treating a CA-MRSA infection which comprises administering to a patient with a CA-MRSA infection an effective amount of cefoxitin and an effective amount of a beta-lactam. In preferred embodiments, the CA-MRSA infection is with a MW2 or USA300 strain and the beta-lactam is a penicillin derivative or cephalosporin.

Another object of the present invention is a method of screening a drug for activity to inhibit PBP4 in *S. aureus* isolates which comprises contacting MW2 or USA300 isolates of *S. aureus* in vitro with a compound to be tested for activity against PBP4, determining a minimum inhibitory concentration level for the compound against MW2 or USA300, and comparing the minimum inhibitory concentration level for the compound with a minimum inhibitory concentration level for oxacillin in an MW2 or an USA300 isolate, wherein the compound is identified as having activity to inhibit PBP4 in *S. aureus* when the minimum inhibitory concentration level for the compound is equal to or less than the minimum inhibitory concentration level for oxacillin. In preferred embodiments, the method of screening employs contact of the compound to be tested with both MW2 and USA300 isolates and the minimum inhibitory concentration level for both is determined.

Another object of the present invention is a topical composition for treating a CA-MRSA infection in a patient which comprises an effective amount of cefoxitin and an effective amount of a beta-lactam in a pharmaceutically acceptable vehicle, wherein said vehicle is suitable for topical application to the skin of a patient with a CA-MRSA infection. In preferred embodiments the CA-MRSA infection is with an MW2 strain or a USA300 strain, and the beta-lactam is a penicillin derivative or cephalosporin. In certain embodiments, the topical composition contains a pharmaceutically acceptable vehicle formulated as an ointment, a cream, a lotion, a paste, a gel, a spray, an aerosol, an oil, or a wound dressing.

BRIEF DESCRIPTION OF THE DRAWINGS

FIG. 2 depicts results of experiments with a TRITON X-100-induced autolysis assay.

DETAILED DESCRIPTION OF THE INVENTION

Figure 1A:
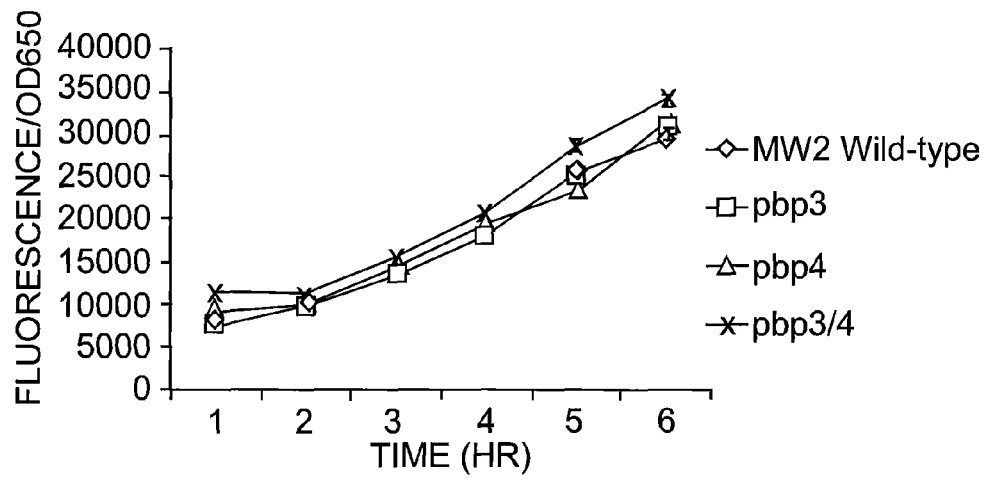
FIG. 1 depicts the expression of $GFP_{uvr}$ driven by pbp2-P1 (FIG. 1A and FIG. 1B, MW2.
FIG. 1E and FIG. 1F, COL) and pbp2-P2 promoters (FIG. 1C and FIG. 1D, MW2.
FIG. 1G and FIG. 1H, COL) in uninduced (FIG. 1A and FIG. 1C, FIG. 1E and FIG. 1G) and induced (FIG. 1B and FIG. 1D, FIG. 1F and FIG. 1H) cultures with 10×MIC oxacillin. Promoter activity was plotted as mean fluorescence/$OD_{650}$ from three clones in triplicates. The experiments were repeated three times, with data from one set shown. The "*" indicates statistical significance of the indicated strain to MW2 at 3-6 hour time points after antibiotic challenge by the paired Student's t-test ($p<0.001$).
Figure 1B:
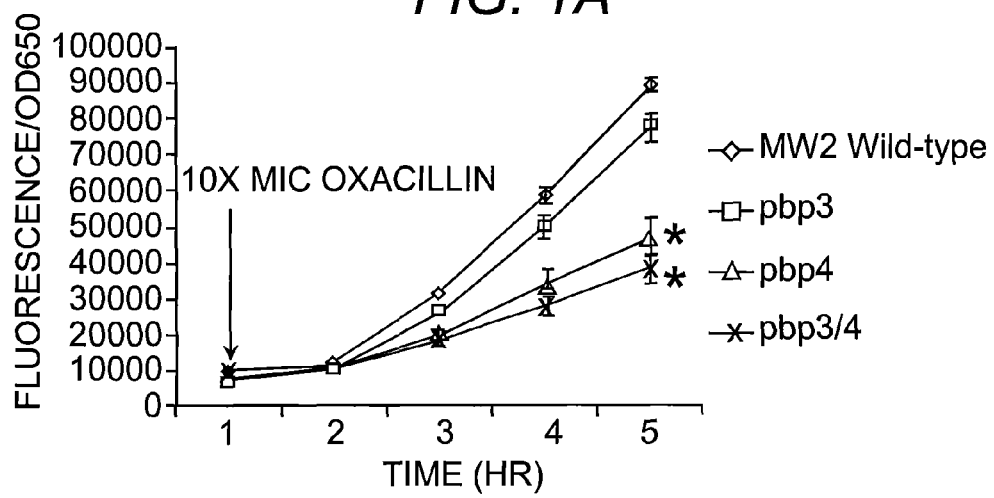
Figure 1C:
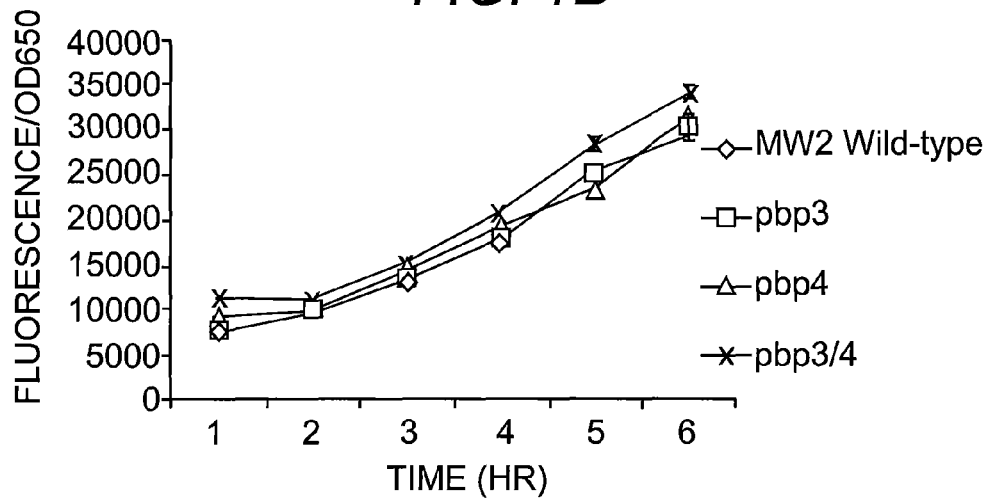
Figure 1D:
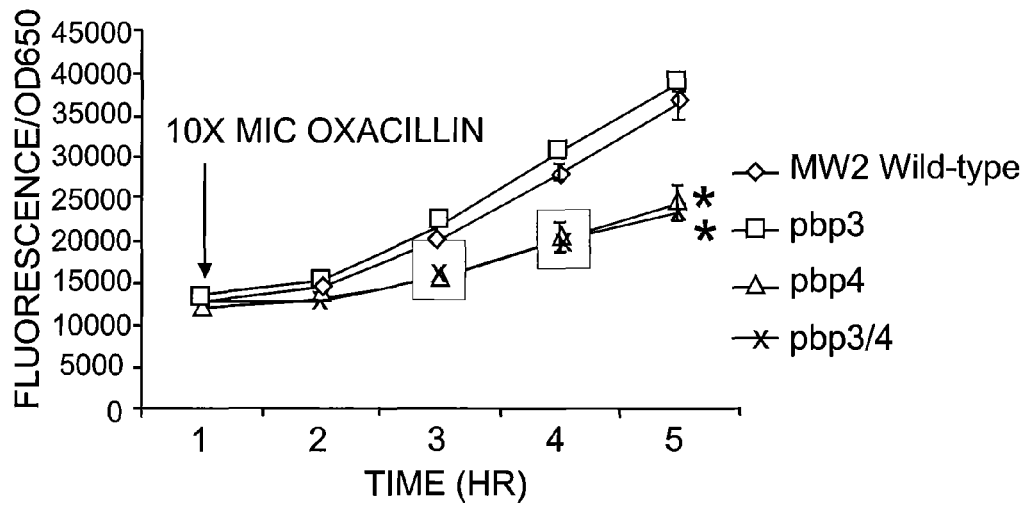
Figure 1E:
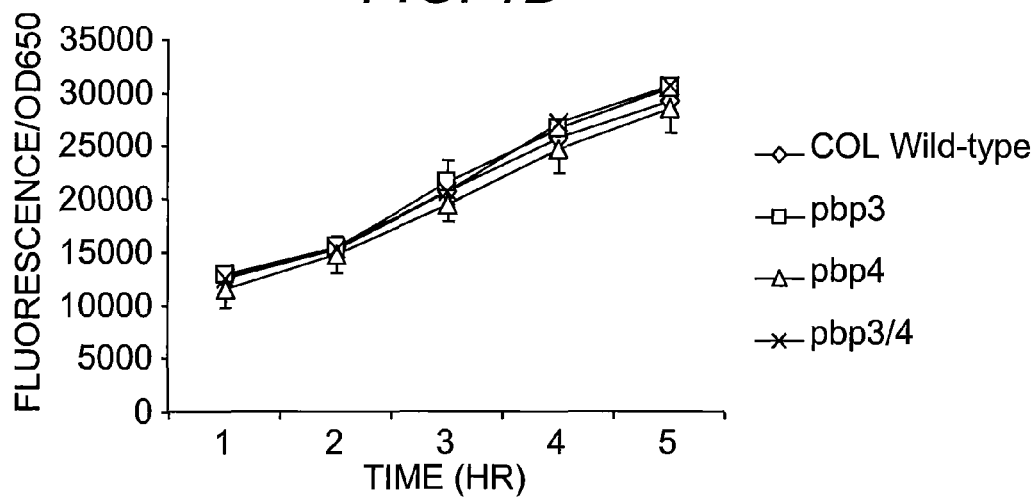
Figure 1F:
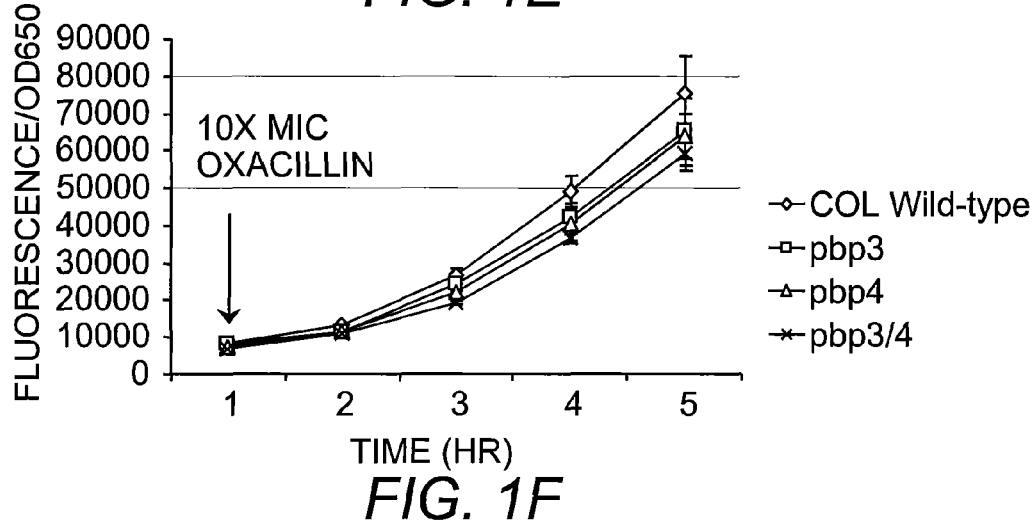
Figure 1G:
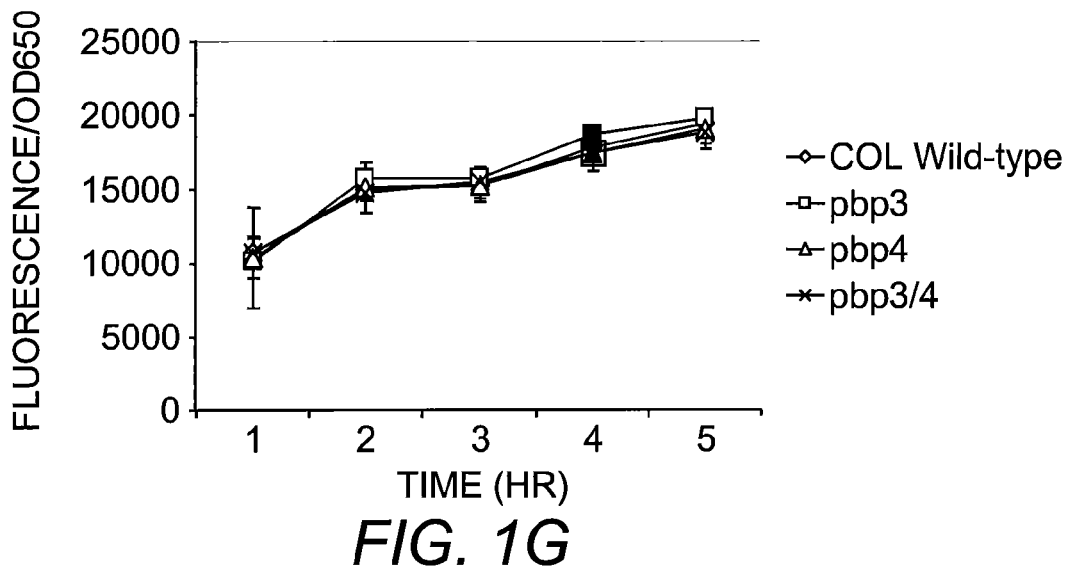
Figure 1H:
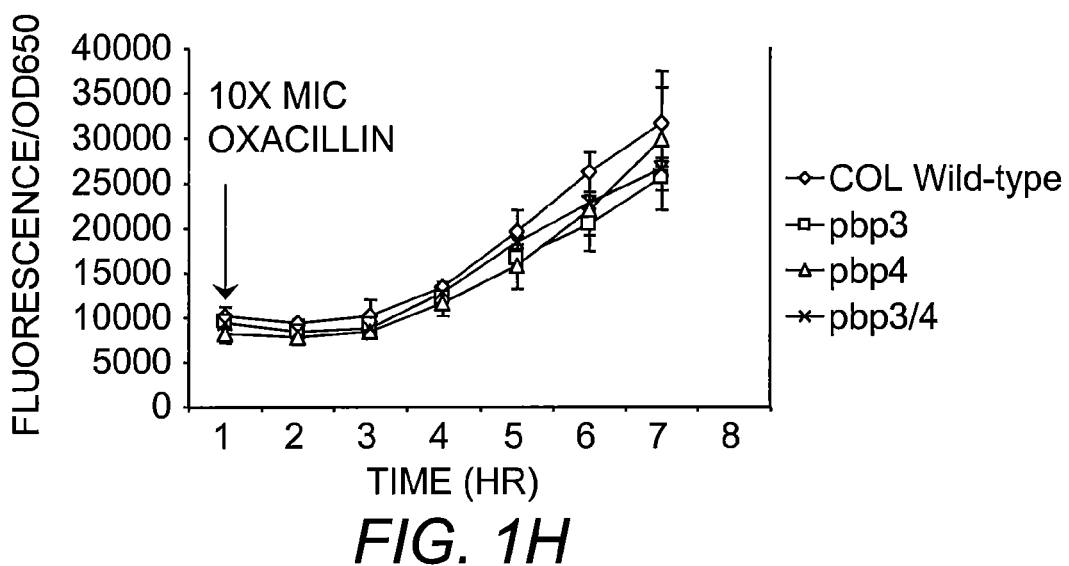

It has been demonstrated that PBP4 has an unexpected role in CA-MRSA resistance. Data show that a loss of pbp4 in CA-MRSA strains leads to a dramatic decrease in oxacillin and nafcillin resistance while the same deletion does not confer a similar phenotype in HA-MRSA strains. Loss of PBP4 has also been shown to have a dramatic impact on PBP2 transcription in cells challenged with oxacillin in CA-MRSA strains but not in HA-MRSA strains. The defect in PBP2 expression likely contributes to resistance, however it was not the only contributing factor to the resistance mechanism, since complementation of pbp2 in trans did not significantly alter β-lactam resistance in pbp4 mutants but complementation of the pbp4 mutant with the pbp4 gene did. Data also have demonstrated that cefoxitin, a β-lactam that binds PBP4 irreversibly, renders CA-MRSA strains as well as clinical isolates from skin and soft tissue infections designated by hospitals as potential CA-MRSA infections, sensitive again to oxacillin. Based on this finding of a role for PBP4 in CA-MRSA, methods of diagnosis and treatment of CA-MRSA have been developed. The diagnostic methods are based on the unique sensitivities of CA-MRSA to certain antibiotics (β-lactams in the presence of an antibiotic that inhibits PBP4 such as cefoxitin, imipenem and cefmetazole)] as well as the identification of CA-MRSA-specific surface markers (biomarkers) which can be targeted by various binding agents to detect the presence of CA-MRSA strains. Additionally, understanding of the unique sensitivities of CA-MRSA to certain antibiotics has resulted in the present invention which encompasses methods for treating CA-MRSA in a patient, as well as methods for screening for compounds to treat CA-MRSA based on the finding that PBP4 plays a role in CA-MRSA sensitivity to β-lactams.

The present invention was described based on a series of experiments examining the biological basis for CA-MRSA strains versus HA-MRSA strains, focusing on the role of PBPs in CA-MRSA and generally in β-lactam resistance. Experiments were first performed using mutants of various PBPs. In-frame deletion mutants of the genes encoding PBP3 (MW1504) and PBP4 (MW0604), pbp3 and pbp4 respectively, were generated in the CA-MRSA strain MW2 and in HA-MRSA strain COL using the temperature-sensitive allelic replacement vector pMAD (Arnaud, M. et al. 2004. *Appl. Environ. Microbiol.* 70:6887-6891). PBP4 was also deleted in the HA-MRSA strains Mu50 and N315 and in the CA-MRSA strain USA300. The PBP4 gene shares a 400-nucleotide intercistronic region with the divergently transcribed abcA (MW0605), encoding an ATP-binding cassette transporter that has been shown to be involved in cell wall metabolism and division (Schrader-Fischer and Berger-Bächi. 2001. *Antimicrob Agents Chemother.* 2001 45 (2): 407-12). Accordingly, using northern blot analysis it was confirmed that the pbp4 deletion did not result in a polar effect in both the upstream (MW0603, tagD, teichoic acid biosynthesis protein D) and the downstream (abcA) genes. Hypersensitivity to oxacillin, cefoxitin and nafcillin was first assessed by comparing minimum inhibitory concentrations for parental and isogenic PBP mutant strains (Table 1). Minimum inhibitory concentrations (MICs) were determined according to the Clinical and Laboratory Standards Institute and are a standard method for defining antibiotic efficacy against different organisms. Bacteria, grown to an $OD_{650}=1$, were added to cation-supplemented Mueller Hinton broth (CSMHB) to achieve a final concentration of $5 \times 10^5$ CFU/ml.

TABLE 1

| Strains | Serotype PFGE | MICs μg/ml | | |
|---|---|---|---|---|
| | | OX[b] | NF[b] | CX[b] |
| MW2 (USA400)wild-type | USA400 | 64 | 16 | 64 |
| MW2 Δpbp3 | USA400 | 64 | 16 | 64 |
| MW2 Δpbp4 | USA400 | 4 | 1 | 64 |
| MW2 Δpbp3/4 | USA400 | 4 | 1 | 64 |
| MW2 Δpbp4::pbp4 | USA400 | 64 | 16 | 64 |
| MW2 ex[a] | USA400 | 128 | 16 | 16 |
| MW2 ex Δpbp3 | USA400 | 128 | 16 | 32 |
| MW2 ex Δpbp4 | USA400 | 2 | 1 | 16 |
| MW2 ex Δpbp3/4 | USA400 | 1 | 1 | 32 |
| USA300 wild-type | USA300 | 64 | 16 | 64 |
| USA300 Δpbp4 | USA300 | 4 | 1 | 64 |
| USA300 Δpbp4::pbp4 | USA300 | 64 | 16 | 64 |
| COL wild-type | USA500 | 256 | 64 | 128 |
| COL Δpbp3 | USA500 | 256 | 64 | 128 |
| COL Δpbp4 | USA500 | 256 | 64 | 128 |
| COL Δpbp3/4 | USA500 | 256 | 64 | 128 |
| N315 wild-type | USA100 | 256 | 64 | 64 |
| N315 Δpbp4 | USA100 | 128 | 64 | 64 |
| Mu50 wild-type | USA100 | 256 | 256 | 256 |
| Mu50Δpbp4 | USA100 | 256 | 256 | 256 |

MW2 ex[a]: MW2 cured of plasmid pMW2
[b]OX = oxacillin; NF = nafcillin; CX = cefoxitin The results showed that expression of pbp4 is essential for β-lactam resistance in CA-MRSA strains (MW2 or USA400 and USA300), but not for HA-MRSA strains (COL, N315 and Mu50). Oxacillin and nafcillin resistance was not altered in pbp3, pbp4 or double mutants of COL, similar to previous studies (Katayama, Y. et al. 2003. *Microb. Drug Resist.* 9:329-336; Pinho, M. G. et al. 2000. *J. Bacteriol.* 182:1074-1079). Remarkably, loss of pbp4 in MW2 and USA300 resulted in a 16-fold reduction in oxacillin and nafcillin MIC (from 64 to 4 μg/ml and from 16 to 1 μg/ml, respectively) while a deletion in pbp3 had no effect. Loss of PBP4 in HA-MRSA strains N315 and Mu50 resulted in minimal or no decrease in MIC values for both oxacillin and nafcillin, similar to strain COL. These data clearly demonstrated differences between CA-MRSA and HA-MRSA that could be exploited toward the development of novel diagnostic tools and therapeutic agents.

The ability of *S. aureus* to survive in the presence of β-lactams relies upon its ability to express PBP2A, the product of mecA. The transglycosylase domain of PBP2 is a second crucial determinant for β-lactam resistance in MRSA strains (Pinho, M. G. et al. 2001. *Proc. Natl. Acad. Sci. USA* 98:10886-10891). Recent data have shown that PBP2 affects expression of mecA and also functions cooperatively with the transpeptidase activity of PBP4 (Gardete, S. et al. 2006. *Microbiology* 152:2549-2558; Leski, T. A. and A. Tomasz. 2005. *J. Bacteriol.* 187:1815-1824). Therefore, northern blot analysis was performed on extracted RNA to assess whether loss of resistance in the pbp4 mutants was due to defective pbp2 or mecA expression. The data showed that a loss of pbp4 diminished the induced expression of pbp2 upon exposure to the cell wall active antibiotics oxacillin and vancomycin in CA-MRSA MW2, but not in HA-MRSA COL. However, the transcript levels of mecA were unaffected in the pbp4 mutants of both MW2 and COL. The defect in induction of pbp2 expression with oxacillin in the pbp4 mutant of MW2 was restored to wild-type levels upon complementation while the empty vector had no effect.

To confirm the effect of pbp4 deletion on pbp2 expression, the P1 (2.9 kb transcript) and P2 (2.2 kb transcript) promoters of pbp2 were fused to a promoterless gfp$_{uvr}$ reporter gene in shuttle plasmid pALC1484. Both P1 and P2 promoters were induced by oxacillin at 10×MIC in MW2, but not in the pbp4 or pbp4/pbp3 mutant, confirming the northern blot data (FIGS. 1A-1D). The differences in GFP values are not simply due to a difference in growth between the wild-type and the mutant strains because the results after 4 hours of induction with oxacillin were virtually identical among all strains. Additionally, differences in GFP values were still apparent even after overnight growth, thus confirming that the disparity was due to a transcriptional defect instead of a growth defect. Differences in the induction of pbp2 after antibiotic challenge were less apparent in pbp4 and pbp4/pbp3 mutants of strain COL (FIGS. 1E-1H) where both P1 and P2 promoters were equally upregulated in the presence of oxacillin and vancomycin in both wild-type and mutant strains.

To exclude chromosomal rearrangement or an ectopic point mutation as the cause for the loss of resistance, the pMAD plasmid was used to reintroduce pbp4 into the chromosome of Δpbp4 and Δpbp3/pbp4 mutants of MW2. Both chromosomally complemented strains, MW2 Δpbp4::pbp4 and USA300 Δpbp4::pbp4 regained wild type levels of oxacillin resistance (Table 1). The same results were also obtained when the ORF encoding PBP4 was cloned in the xylose inducible system pEPSA5, while the empty vector did not have any effect. However, the expression of PBP2 or PBP2A in pEPSA5 did not alter the MIC in either pbp4 or pbp3/4 mutants of MW2 and USA300. Thus, the reduction in oxacillin resistance in the pbp4 mutant of MW2 and USA300 was not fully attributable to pbp2 because expression of pbp2 from the inducible plasmid pEPSA5 did not restore oxacillin resistance to the pbp4 mutant, with no changes in MICs (4 μg/ml). Furthermore, to exclude possible polar effects due to genetic manipulation of the ORFs encoding PBP3 and PBP4, transcription profiles of genes upstream and downstream of both ORFs were examined in MW2, revealing no significant alterations between the wild type and the mutants.

The HA-MRSA strain COL and the CA-MRSA strain MW2 have substantially different regulations of mecA. Both strains lack the gene encoding mecI, a repressor of mecA expression. However MW2 carries the blaIRZ operon on the plasmid pMW2, which codes for the penicillinase-regulatory gene blaI, the membrane sensor gene blaR and the penicillinase gene blaZ; blaI was previously found to regulate in trans the expression of mecA (McKinney, T. K. et al. 2001. *J. Bacteriol.* 183:6862-6868). For the MW2 strain, the plasmid pMW2, which is responsible for the tight regulation of mecA, was first cured to generate a derivative strain MW2 ex. The CA-MRSA strain MW2 ex, cured of its plasmid pMW2, resulted in constitutive expression of mecA, similar to what has been found with COL. In the complemented strain obtained by reintroducing the plasmid pMW2 into MW2 ex, the expression of mecA was again tightly regulated and repressed unless oxacillin was added to induce expression. Loss of pbp4 in MW2 ex, with or without concomitant loss of pbp3, led to a more substantial decrease in oxacillin resistance than in MW2, with a 64-fold reduction in oxacillin MIC for the pbp4 mutant (from 128 to 2 μg/ml in MW2 ex vs. 64 to 4 μg/ml in MW2) and a 128-fold reduction for the pbp3/4 double mutants (from 128 to 1 μg/ml in MW2 ex vs. 64 to 1 μg/ml in MW2), respectively (Table 1). Thus, the plasmid pMW2 does not contribute significantly to oxacillin or β-lactam resistance in CA-MRSA strains.

Figure 2A:
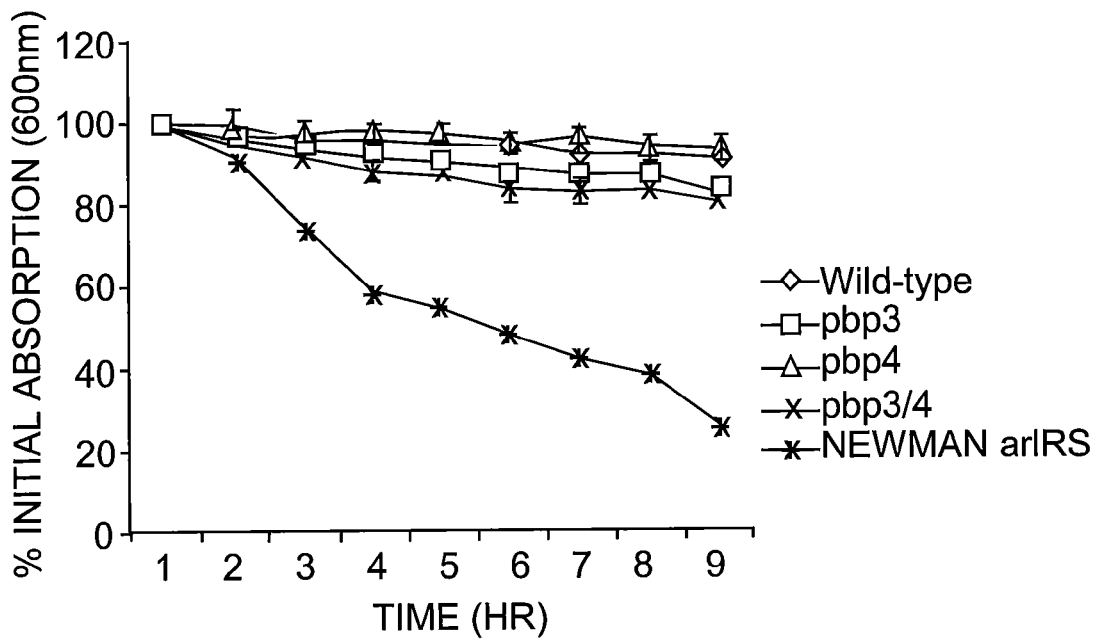
FIG. 2A depicts results under static conditions. After adding TRITON X-100 (0.05%), autolysis of mid-exponential cultures was determined at 30° C. without shaking, by serial OD measurements. The arlRS mutant strain Newman was used as a positive control.
Figure 2B:
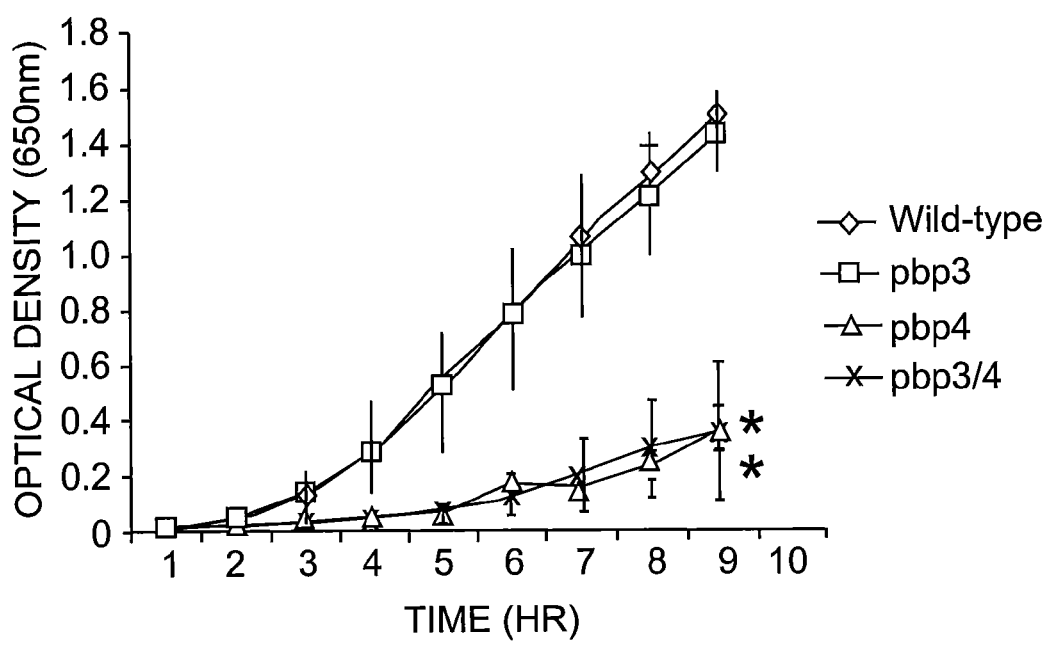
FIG. 2B depicts results on growing cells of MW2 and its isogenic mutants. Overnight cultures, diluted to an $OD_{650}$ of 0.1 in Mueller Hinton Broth (Becton Dickinson) supplemented with 25 µg/ml $Ca^{+2}$, 12.5 µg/ml $Mg^{+2}$, and 2% NaCl (designated CSMHB) with 0.05% TRITON X-100, were grown at 37° C. with shaking. The "*" indicates statistical significance of pbp4 and pbp3/4 mutants to MW2 at 4-9 hour time points by the paired Student's t-test ($p<0.001$).

To assess whether or not loss of pbp4 and hypersensitivity to β-lactams was due in part to an effect on autolytic regulatory genes and/or increased murein hydrolase activity, northern blot analysis was conducted with DNA probes specific for the following genes: sarA, sarR, sarT, sarS, mgrA, atl, lytM, lytN, lysR, lytSR, cidABC, and lrgAB. Besides a minor difference in sarA transcription in all pbp mutants, all other transcript levels tested were similar between wild type and isogenic mutant strains. Zymogram analysis also did not reveal increased autolysis, with similar murein hydrolase activities between MW2 and all pbp mutants. The effect of the non-ionic detergent TRITON X-100 on static and actively growing cells also was examined. No differences in optical densities were observed between wild type and the mutants in static cultures exposed to 0.05% TRITON X-100 at 30° C. under static conditions (FIG. 2A); the two-component system arlRS mutant in the Newman background was used as a positive control for increased autolysis. In growing cultures at 37° C. with TRITON X-100, both pbp4 and pbp4/pbp3 mutants showed a significantly slower rise in optical density (OD) as compared with the wild type or complemented pbp4 mutant. This difference in the rise of OD between static and actively growing cultures is more consistent with a defect in cell wall biosynthesis than augmented autolytic activity (FIG. 2B).

Figure 3:
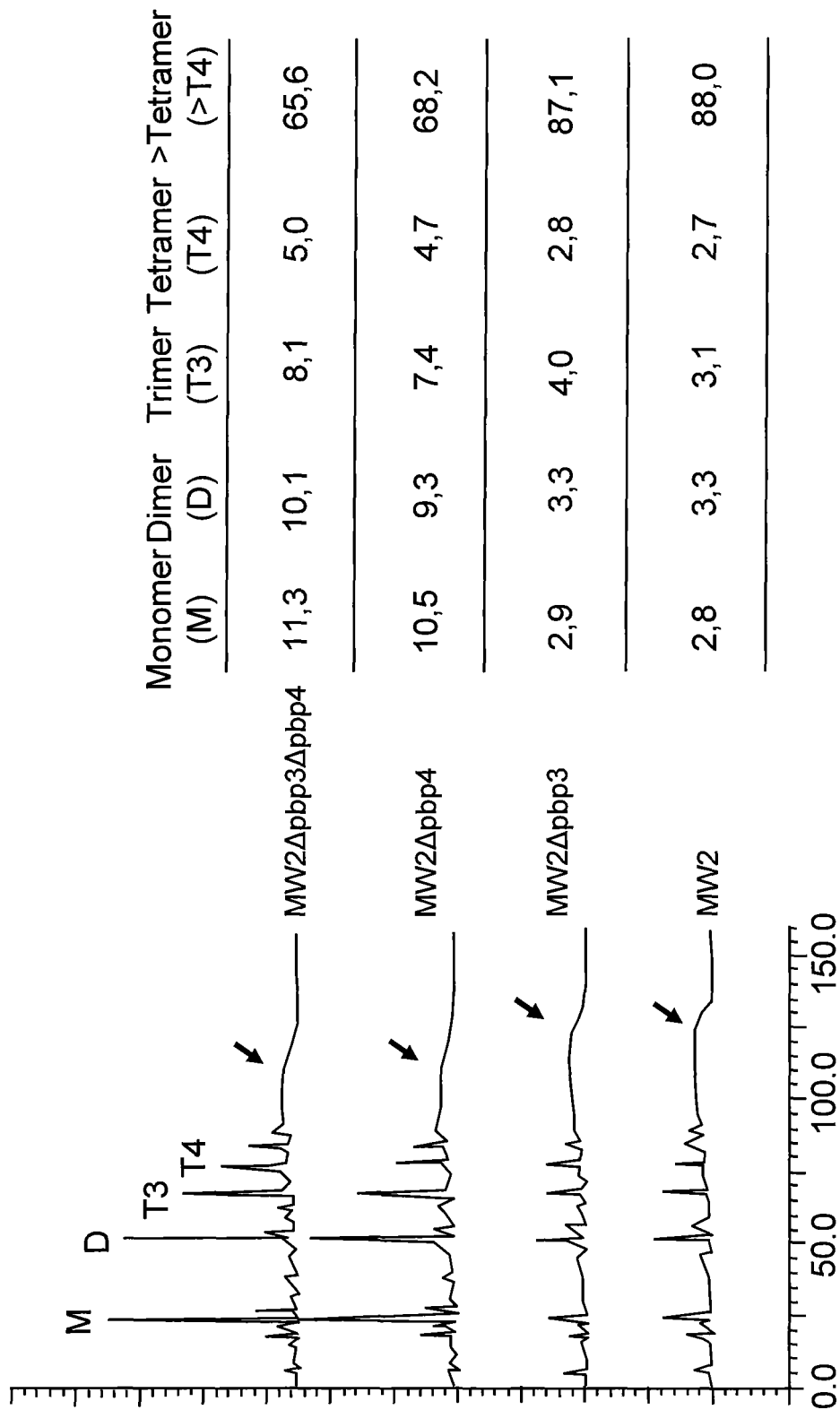
FIG. 3 depicts the effect of deleting pbp3 and pbp4 on MW2 peptidoglycan composition. The muropeptide composition of peptidoglycan was analyzed by HPLC. The identity of each peak was assigned based on the specific retention time in comparison to previously identified peaks of COL strain, with arrows pointing to highly crosslinked muropeptides present in MW2 and pbp3 mutant but that are reduced in pbp4 and pbp3/pbp4 mutants. Quantification of the area of eluted peaks was carried out using Shimadzu LC solution software, with the data presented as percentage of the total identified peaks.

Previous studies have linked loss of PBP4 to a reduction in peptidoglycan cross-linking in methicillin-susceptible *S. aureus* (MSSA) strains, MRSA COL, and glycopeptide-resistant *S. aureus* strains (Sieradzki, K. et al. 1999. *J. Biol. Chem.* 274:18942-18946). HPLC elution profiles of muropeptide species released by muramidase digest of peptidoglycan from MW2 and its pbp mutants (FIG. 3) showed that there was an increase of monomers, dimers, trimers and tetramers and a concomitant reduction in the proportion of highly cross-linked muropeptides (>tetramer) in pbp4 mutants but not in pbp3 mutants.

Experiments were then performed to address whether a loss of PBP4 would have an effect on cell wall morphology upon β-lactam challenge. Using electron microscopy for analysis, it was shown that in the absence of β-lactams, no major differences were spotted. Upon challenge with 1×MIC oxacillin, abnormal morphological features, including abnormal shape, incomplete septum formation, rough cell wall surfaces, and irregularly placed septa were seen in all strains. Therefore, a mutation in pbp4 did not result in a specific morphological defect in CA-MRSA strains.

Although PBP4, similar to PBP2A, binds with low affinity to many β-lactams, PBP4 binds cefoxitin, a semi-synthetic β-lactam derived from cephamycin C, with high affinity (Nair, S. R. and C. E. Cherubin. 1978. *Antimicrob. Agents Chemother.* 14:866-875). With data (described above) demonstrating a role for PBP4 in the mechanism of resistance in CA-MRSA strains, experiments were performed to test for a potential synergistic effect of cefoxitin (0.25×MIC) in combination with oxacillin by determining the MIC of oxacillin with CA-MRSA and HA-MRSA strains (Table 2).

TABLE 2

| Strains | # clones tested | OX[a] 48 hr | CX[a] 48 hr | OX + ¼ MIC CX 24 hr | OX + ¼ MIC CX 48 hr | OX + ¼ MIC CF[a] 48 hr |
|---|---|---|---|---|---|---|
| MW2 (USA400) CA-MRSA | 3 | 64 | 64 | <1 | <1 | 64 |
| USA300 CA-MRSA | 3 | 64 | 64 | <1 | <1 | 64 |
| COL HA-MRSA | 3 | 256 | 128 | 32 | 64 | NA |
| MRSA252 HA-MRSA | 3 | 256 | 128 | 64 | 128 | NA |
| Mu50 HA-MRSA/VISA | 3 | 256 | 256 | 128 | 256 | NA |
| CA-MRSA Strains | 30 | 64[b] | 64[b] | <1 | <1 | NA |
| CA-MRSA from CSSTI[c] | 30[d] | 64[b] | 64[b] | <1 | <1 | NA |
| HA-MRSA Strains | 30 | 256[b] | 128[b] | 32[b] | 64[b] | NA |

[a] OX = oxacillin; CX = cefoxitin; CF = cefuroxime.
[b] MIC data for all clinical isolates were reported as median values in ug/ml from at least three independent experiments.
[c] denotes complicated skin and soft tissue infections
[d] Two CSSTI isolates showed MIC values for this combination higher than the rest of tested strains (MIC oxacillin = 4 µg/ml compared to 1 µg/ml, still several times below the maximum achievable concentration in vivo).

Figure 4A:
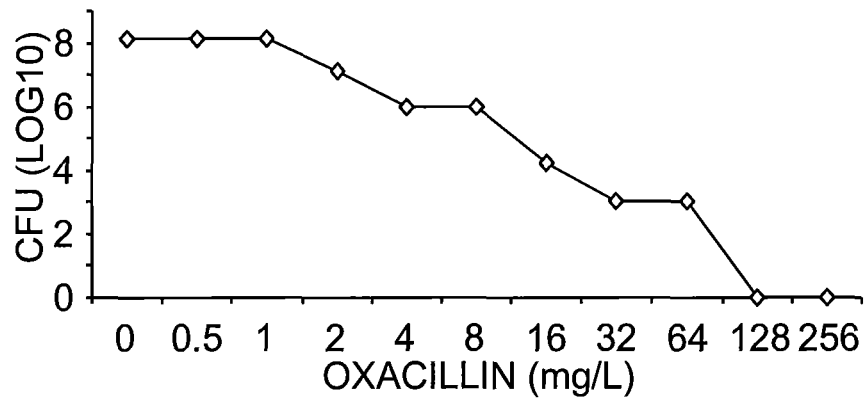
FIG. 4 depicts a population analysis of susceptibility to oxacillin (FIG. 4A), cefoxitin (FIG. 4B) and oxacillin combined to one fourth the MIC of cefoxitin (FIG. 4C) for the wild-type strain MW2. Antibiotic susceptibilities of strains were determined in overnight cultures plated on agar containing different concentrations of oxacillin, cefoxitin or ¼ the MIC of cefoxitin with two-fold dilution of oxacillin and incubated at 37° C. for 48 hours.
Figure 4B:
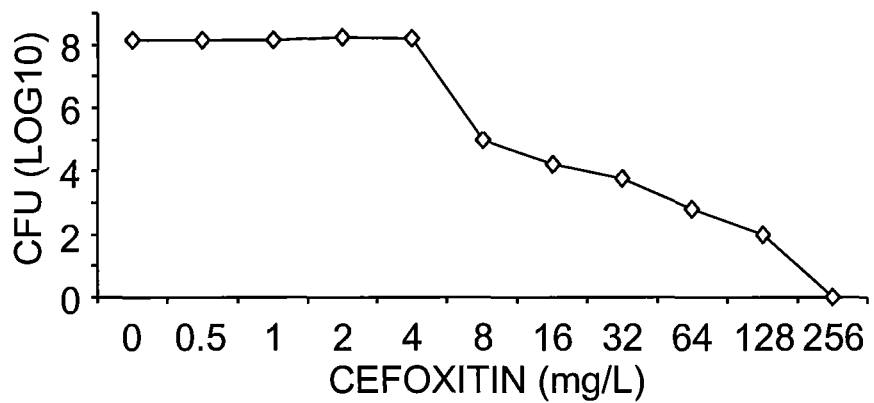
Figure 4C:
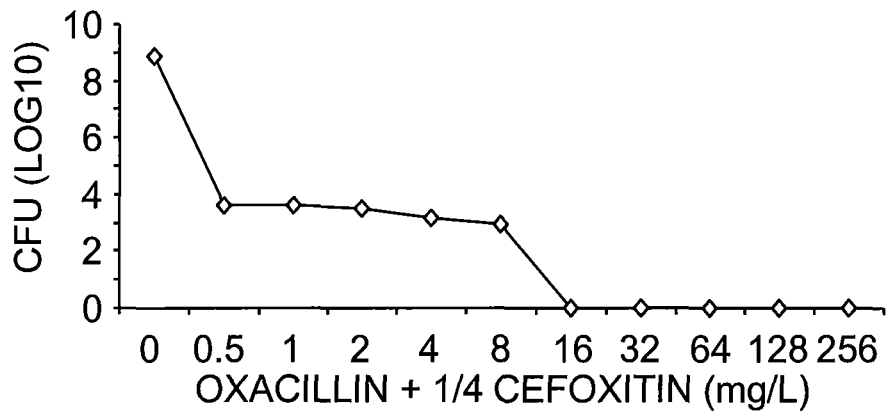

As can be seen from the data presented in Table 2, oxacillin resistance was minimally altered by the presence of cefoxitin in HA-MRSA strains COL and MRSA252 and VISA strain Mu50. In contrast, a synergistic inhibitory effect was seen with cefoxitin in CA-MRSA strains MW2 and USA300, with both strains being unable to grow at <1 µg/ml of oxacillin at both the 24 and 48-hour time points. The minimum bactericidal concentration (MBC) for oxacillin, cefoxitin, and oxacillin combined to one fourth the MIC of cefoxitin in both CA- and HA-MRSA strains was also tested (Table 3). The MBC of oxacillin for both MW2 and USA300 was 256 µg/ml, while that for cefoxitin alone was >256 µg/ml. Synergy between the two drugs was also demonstrated, showing the MBC for oxacillin with one fourth the MIC of cefoxitin to be <1 µg/ml for both MW2 and USA300 (Table 3). Population analysis of susceptibility to oxacillin, cefoxitin, and oxacillin combined to one fourth the MIC of cefoxitin to detect trends and potential for developing resistance was also evaluated (FIG. 4), demonstrating the synergistic inhibitory effect of cefoxitin and oxacillin on the CA-MRSA strain MW2, with the MIC for oxacillin dropping to a level that is still clinically achievable, from 128 to 0.5 µg/ml.

TABLE 3

| Strains | # Clones Tested | OX[a] 48 hr | CX[a] 48 hr | OX + ¼ MIC CX 48 hr |
|---|---|---|---|---|
| MW2 (USA400) CA-MRSA | 3 | 256 | >256 | <1 |
| USA300 CA-MRSA | 3 | 256 | >256 | <1 |
| COL HA-MRSA | 3 | >256 | >256 | >256 |
| MRSA252 HA-MRSA | 3 | >256 | >256 | >256 |
| Mu50 HA-MRSA/VISA | 3 | >256 | >256 | >256 |

[a] OX = oxacillin; CX = cefoxitin
[b] MIC data for all clinical isolates were reported as median values in ug/ml from at least three independent experiments.

To assess the efficacy of the synergistic combination of oxacillin and cefoxitin on other CA-MRSAs, 200 MRSA isolates, blinded with respect to the origin, were screened. Analysis of the Type IV SCCmec element, virtually identical between MW2 and USA300, allowed for identification of four genes conserved in the CA-MRSA background, but not in other known MRSA genomes. These four genes therefore served as biomarkers that could be used to distinguish CA-MRSA strains from HA-MRSA strains. PCR of chromosomal DNAs with oligonucleotides specific for mecA, pvl (Lina, G. et al. 1999. *Clin. Infect. Dis.* 29:1128-1132) and the four specific genes for CA-MRSAs (MW0042/USA300_0041; MW0043/USA300_0042; MW0046/USA300_0045; and MW0047/USA300_0046) identified 30 isolates positive for these genes. All 30 isolates exhibited the synergistic inhibitory effect of cefoxitin and oxacillin, with 27 strains (90%) unable to grow at <1 µg/ml of oxacillin after 24/48 hours while the remaining three grew at 1, 4 and 8 µg/ml of oxacillin or lower with 0.25×MIC cefoxitin after 48 hours (Table 2). The 30 HA-MRSA isolates, that tested negative for the above genes (but positive for mecA), grew in oxacillin ranging from 4 to 128 µg/ml (median values at 32 and 64 µg/ml at 24 and 48 hrs, respectively) in the presence of cefoxitin. The code was subsequently broken, confirming that all 30 isolates, designated as CA-MRSA, were from patients with primary skin infections and annotated by the donating hospital as CA-MRSA while the other were blood isolates designated as HA-MRSA. Therefore, these data demonstrated not only the utility of a combined treatment of oxacillin and cefoxitin but moreover the utility of using genetic biomarkers for screening MRSA strains as being either CA-MRSA or HA-MRSA. The synergistic inhibitory activity of the combined treatment also was further tested on 30 MRSA isolates from complicated skin and soft tissue infections, with CA-MRSA being the most common etiologic agent. The MICs for cefoxitin for all strains were tested, then the median value was calculated and one fourth of it was used to test the synergistic inhibitory activity with oxacillin. The MIC values for oxacillin for 28 of them were <1 µg/ml when one fourth the MIC of cefoxitin was added. Two isolates presented slightly higher values, with a MIC of 4 µg/ml, which was found to be a consequence of higher resistance to cefoxitin.

When considered together, the results clearly demonstrated that PBP4 is a key element in β-lactam resistance in CA-MRSA strains, and that mecA is not the sole determinant for oxacillin resistance in these isolates. Accordingly, cefoxitin, which binds tightly to PBP4, can be used in combination with synthetic penicillins or β-lactams to treat CA-MRSA infections. Moreover, understanding the genetic determinants that account for a difference in resistance between CA-MRSA and HA-MRSA strains is an important finding that can be used to develop new diagnostic methods for *S. aureus* infections and to develop new treatment regimens for *S. aureus* infections.

Current screening methods for MRSA infections are unable to discriminate between HA-MRSA and CA-MRSA. Such methods include the OXOID Penicillin Binding Protein (PBP2A) Latex Agglutination assay (Oxoid Ltd., Hampshire, U.K.), the BBL CHROMager assay (Becton Dickinson, Franklin Lakes, N.J.), and new PCR diagnostic tests based on the mecA gene sequence (Becton Dickinson, Franklin Lakes, N.J.; Cepheid, Sunnyvale, Calif.). Because these tests cannot distinguish CA-MRSA from HA-MRSA, patients may not be afforded the opportunity to receive treatment targeted to their particular type of infection. Since it is known that CA-MRSA differs from HA-MRSA in its response to antibiotics (Jung et al. 2006. *J. Microbiol.* 44 (3):336-43), the inability to discriminate between the two types of MRSA infections could lead to dire consequences for the patient, even death.

With the understanding provided by the results of the experiments described herein, it is now understood that CA-MRSA can be discriminated from HA-MRSA infection in a patient through use of unique biomarkers of CA-MRSA strains. In the context of the present invention, the term "biomarker" refers to unique substances that when detected in a biological media collected from a patient suspected of having a particular disease or condition are indicative of the presence of a specific disease or condition in the patient. In the present invention, the unique substances would include but not be limited to genes or gene products that are detected in cells or tissues of a patient. As described above, four specific genes (MW0042/USA300_0041, MW0043/USA300_0042, MW0046/USA300_0045, and MW0047/USA300_0046) have been identified as being unique to CA-MRSA strains. Therefore, the present invention is a biomarker for CA-MRSA infection in a patient which comprises these four genes or gene products. One of skill would also understand, however, that the present invention would also encompass application of the methods to derivative CA-MRSA strains, ones that may arise due to spontaneous mutations that occur as well as mutations that might be intentionally produced. Therefore, the present invention would include application to derivative strains of USA300 and MW2 that may be identified. In another embodiment, therefore, the present invention is a biomarker for CA-MRSA infection in a patient wherein the biomarker comprises mutated genes or gene products of USA300 and MW2.

Additionally, the present invention is a method of diagnosing CA-MRSA. The diagnosis can be through detection of one or more CA-MRSA-specific genetic or protein markers. Alternatively, the methods of diagnosis can be based upon measurement of bacterial growth in the presence of cefoxitin and oxacillin.

In accordance with one embodiment of the invention, CA-MRSA is diagnosed based upon MIC levels. Such a diagnosis is carried out by obtaining a blood, tissue or organ sample from a patient suspected of having CA-MRSA and contacting the sample with cefoxitin and oxacillin in vitro to determine a MIC level of oxacillin in the presence of a less than minimum inhibitory concentration (sub-MIC) of cefoxitin. The sensitivity of oxacillin is then compared with the MIC level of oxacillin in the presence of a sub-MIC level of cefoxitin against strains MW2 and USA300, which are typically at <1-2 microgram per milliliter. If the minimum inhibitory concentrations of the combined testing of oxacillin and cefoxitin in the sample from the patient are similar (i.e. at or near 1-2 microgram per milliliter then the patient is diagnosed as having a CA-MRSA infection. In patients with HA-MRSA infection, however, the MIC level to oxacillin in the presence of a sub-MIC level of cefoxitin is typically higher than 32 micrograms per milliliter, similar to COL, MRSA252 and Mu50 strains. Such diagnostic testing based on MIC is routinely carried out in the art and any suitable format can be employed including plate and liquid culturing techniques.

In accordance with another embodiment of the invention, a CA-MRSA infection is diagnosed based upon the presence or expression of one or more CA-MRSA-specific biomarkers. In one embodiment, the presence or expression of one or more CA-MRSA-specific biomarkers is assessed by detecting the presence or level of a nucleic acid encoding the marker by PCR or real-time PCR (with or without a molecular beacon) in a sample, e.g., a blood sample, or the presence or level of the protein itself. Detection of a CA-MRSA-specific biomarker involves contacting a biological sample with a compound or an agent capable of binding the biomarker. A CA-MRSA-specific biomarker is defined as a nucleic acid or protein specifically present or expressed in CA-MRSA, which is not present or expressed in HA-MRSA. Desirably, CA-MRSA-specific biomarkers are found in all isolates of CA-MRSA. In particular embodiments, CA-MRSA-specific biomarkers are present or expressed in both MW2 (USA400) and USA300 isolates. As disclosed herein, exemplary CA-MRSA-specific biomarker genes or gene products include MW0042 and its homolog USA300_0041, MW0043 and its homolog USA300_0042, MW0046 and its homolog USA300_0045, and MW0047 and its homolog USA300_0046. Sequence analysis indicates that MW0042 and USA300_0041 are localized on the cell membrane of MW2 and USA300 isolates, respectively, whereas MW0043, USA300_0042, MW0046 (an HNH endonuclease), USA300_0045 (an HNH endonuclease), MW0047 and USA300_0046 are found in the bacterial cytoplasm. The amino acid and nucleotide sequences of these exemplary CA-MRSA-specific biomarkers are set forth in Table 4.

TABLE 4

| CA-MRSA-Specific Marker | Source | Nucleotide Sequence Accession No.[a] | SEQ ID NO: | Amino Acid Sequence Accession No.[a] | SEQ ID NO: |
|---|---|---|---|---|---|
| MW0042 | MW2 | NC_003923 (51815 ... 52864) | 1 | NP_644857 | 2 |
| MW0043 | MW2 | NC_003923 (53482 ... 54972) | 3 | NP_644858 | 4 |
| MW0046 | MW2 | NC_003923 (56853 ... 57224) | 5 | NP_644861 | 6 |
| MW0047 | MW2 | NC_003923 (57354 ... 57974) | 7 | NP_644862 | 8 |
| USA300_0041 | USA300 | NC_007793 (51298 ... 52389) | 9 | YP_492761 | 10 |
| USA300_0042 | USA300 | NC_007793 (53117 ... 54607) | 3 | YP_492762 | 4 |
| USA300_0045 | USA300 | NC_007793 (56488 ... 56859) | 5 | YP_492765 | 6 |
| USA300_0046 | USA300 | NC_007793 (56988 ... 57608) | 7 | YP_492766 | 8 |

[a]Accession No. are from the GENBANK database.

With the exception of MW0042 and USA300_0041, the nucleic acid and amino acid sequences of the CA-MRSA-specific biomarkers are 100% identical between the MW2 and USA300 isolates. Specifically, USA300_0041 has an addition 42 nucleotides at its 5' end as compared to MW0042. However, the remaining nucleotide sequences encoding MW0042 and USA300_0041 are 100% identical.

An example of an agent for binding and detecting the presence or expression of a CA-MRSA-specific biomarker is a nucleic acid probe capable of hybridizing to a nucleic acid molecule encoding a CA-MRSA-specific biomarker (e.g. genomic DNA or mRNA). The nucleic acid probe can be, for example, an oligonucleotide which is complementary to any of the nucleotide sequences disclosed in Table 4, or portions thereof. The term probe, as defined herein, is meant to encompass oligonucleotides from ten to twenty-five base pairs in length, but longer sequences can be employed. In particular embodiments, a probe of the invention is also suitable as a primer for amplification of a nucleic acid molecule encoding a CA-MRSA-specific marker. Exemplary probes/primers for the amplification of MW0042 (USA300_0041), MW0043 (USA300_0042), MW0046 (USA300_0045) and MW0047 (USA300_0046) sequences are set forth herein in Table 5 and Example 12. Analysis of 100 clinical isolates of each of CA-MRSA and HA-MRSA, indicated that these primers generate amplicons from CA-MRSA nucleic acids only and not from HA-MRSA.

TABLE 5

| CA-MRSA-Specific Marker | Primer | Sequence (5' → 3') | SEQ ID NO: |
|---|---|---|---|
| MW0042 USA300_0041 | Forward | TGATGTAACAGTTGAGGTTTATGAAGATT | 11 |
| | Reverse | CTTTGTAACTAATCTTTTTTGCGTTTTG | 12 |
| MW0043 USA300_0042 | Forward | GCGTGCATTGAAATTCATGTACC | 13 |
| | Reverse | CCAAAGAATAATAAACATGCTGTAGTCA | 14 |
| MW0046 USA300_0045 | Forward | GAAAGAAATCAGGCATTAAGAAATGAAG | 15 |
| | Reverse | TTATTTGCTATTATAATTAACTATTTTGGT | 16 |
| MW0047 USA300_0046 | Forward | CAGGTATTGGAGAAGACTTGCTGG | 17 |
| | Reverse | ATTAACGATAGGCATGATTTCTTCATC | 18 |

An example of an agent for binding and detecting a CA-MRSA-specific biomarker protein is an antibody capable of binding to the biomarker protein (e.g., the membrane protein MW0042). Accordingly, the present invention also provides antibodies raised against each of the biomarkers disclosed in Table 4, or portions thereof. CA-MRSA-specific biomarker proteins can be expressed using conventional expression systems, purified and used to immunize an animal for antibody production. Antibodies can be polyclonal, or more desirably, monoclonal and can be produced by any conventional method in the art. For example, monoclonal antibodies can be prepared using any technique which provides for the production of antibody molecules by continuous cell lines in culture. These include, but are not limited to, the hybridoma technique, the human B-cell hybridoma technique, and the EBV-hybridoma technique (Kohler et al. 1975. *Nature* 256:495-497; Kozbor et al. 1985. *J. Immunol. Methods* 81:31-42; Cote et al. 1983. *Proc. Natl. Acad. Sci.* 80:2026-2030; Cole et al. 1984. *Mol. Cell. Biol.* 62:109-120).

An intact antibody, antibody derivative, or a fragment thereof (e.g., Fab or F(ab')$_2$) can be used. In certain embodiments, the antibody is labeled. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a protein or DNA probe with biotin such that it can be detected with fluorescently labeled streptavidin. In some embodiments, the antibody is labeled by adsorption to latex beads for use in a rapid latex agglutination assay with CA-MRSA, wherein agglutination is indicative of the presence of CA-MRSA. In addition, the presence of the surface antigen MW0042 can be detected by, e.g., an aerosolized immunoassay which provides a colorimetric readout to diagnose CA-MRSA on the surface of the skin.

Suitable antibodies or primers/probes useful for biomarker binding and detection can be routinely generated by the skilled artisan from biomarker sequences set forth herein in Table 4. As such, one embodiment of the invention embraces the detection of one or more of the CA-MRSA-specific nucleic acid biomarkers set forth in SEQ ID NO:1, SEQ ID NO:3, SEQ ID NO:5, SEQ ID NO:7 or SEQ ID NO:9. In another embodiment, the invention embraces the detection of one or more of the CA-MRSA-specific protein biomarkers set forth in SEQ ID NO:2, SEQ ID NO:4, SEQ ID NO:6, SEQ ID NO:8 or SEQ ID NO:10.

The detection methods described herein can be used to detect the presence of biomarker nucleic acids or biomarker protein in a biological sample in vitro as well as in vivo. In vitro techniques for detection of biomarker RNA include, but are not limited to, northern hybridization and in situ hybridization. In vitro techniques for detection of biomarker DNA include, but are not limited to, Southern hybridization and in situ hybridization. In vitro techniques for detection of biomarker protein include, but are not limited to, agglutination assays, enzyme-linked immunosorbent assays (ELISAs), western blots, immunoprecipitations, and immunofluorescence assays. Alternatively, a biomarker protein can be detected in vivo in a subject by introducing into the subject a labeled antibody against the biomarker protein. For example, the antibody can be labeled with a radiotracer or radiopharmaceutical, or fluorescent or other imaging marker whose presence and location in a subject can be detected by standard imaging techniques. In particular, given that MW0042 (USA300_0041) is localized to the plasma membrane, this protein can be readily detected both in vivo and in vitro, with little sample preparation. In embodiments embracing the detection of MW0043 (USA300_0042), MW0046 (USA300_0045) or MW0047 (USA300_0046) protein biomarkers, phage lysin can be incorporated into the assay to instantly lyse the *S. aureus* cells, thereby releasing the intracellular proteins. An example of a phage lysin suitable for use is the lysin (LysK) from staphylococcal phage K. Indeed, recombinant LysK was found to inhibit a range of different species of staphylococci isolated from bovine and human infection sources, including methicillin-resistant *Staphylococcus aureus* (O'Flaherty et al. 2005. *J. Bacteriol.* 187:7161-7164).

For nucleic acid-based detection it is frequently desirable to amplify the nucleic acid sample prior to hybridization. One of skill in the art will appreciate that methods of amplifying nucleic acids are well-known in the art. Such amplification methods include, but are not limited to polymerase chain reaction (PCR) (Innis et al. 1990. *PCR Protocols. A guide to Methods and Application*. Academic Press, Inc., San Diego), real time PCR (RT-PCR), semi-quantitative RT-PCR, ligase chain reaction (LCR) (Wu and Wallace. 1989. *Genomics* 4:560; Landegren et al. 1988. *Science* 241:1077; Barringer et al. 1990. *Gene* 89:117), transcription amplification (Kwoh et al. 1989. *Proc. Natl. Acad. Sci. USA* 86:1173), and self-sustained sequence replication (Guatelli et al. 1990. *Proc. Nat. Acad. Sci. USA* 87:1874).

In the present invention, the presence of the CA-MRSA biomarkers are identified in samples taken from a patient suspected of having a CA-MRSA infection. In the context of the present invention, a sample is any fluid, cell, or tissue, living or dead. Those of skill in the art will recognize that the samples to be analyzed by the methods of the present invention can come many sources including but not limited to blood, skin cells, biopsy tissue, or similar biological samples. The sample can be obtained by a physician or healthcare professional in a hospital or other healthcare environment in traditional manners. Samples would then be prepared for analysis using methods well know to those of skill in the art and dependent on the method of detection to be used.

In addition to diagnostic methods for CA-MRSA, the present invention embraces methods of treating CA-MRSA infections which include administering to a patient having or suspected of having a CA-MRSA infection in their bloodstream, internal organs or tissues an effective amount of cefoxitin (or other PBP inhibitors including imipenem or cefmetazole) and an effective amount of a beta-lactam antibiotic, including but not limited to penicillin, synthetic penicillin, and cephalosporins or their derivatives. In a preferred embodiment, the CA-MRSA infection is with either a MW2 or USA300 strain of CA-MRSA. In the context of the present invention, "an effective amount" is defined as an amount of the drug capable of inhibiting growth of *S. aureus*. The amount of drug that inhibits growth of *S. aureus* can be determined by a variety of means well known to those of skill in the art including determining a MIC level for a drug in vitro, as described in the present invention. For example, the MIC level of oxacillin for CA-MRSA strains USA300 and MW2 is typically less than 1 μg/ml while that of HA-MRSA strains is greater than 32 μg/ml when the drug is in the presence of a sub-MIC level of cefoxitin which is typically used at a ¼ MIC level. For any drug that is currently approved for use to treat infections in humans, one of skill could also determine "an effective amount" based on the approved dose ranges for the drug, doses which are commonly listed in sources such as regulatory agency approved drug labeling. It should also be noted that the determination of a MIC level in vitro with isolates of organisms is a well-established method for determining which type of drug to use in patients and is thus directly related to the potential efficacy of a drug.

β-lactam antibiotics are a broad class of well-known antibiotics which includes penicillin derivatives (both synthetic and semi-synthetic penicillins), cephalosporins, monobactams, carbapenems and β-lactamase inhibitors, i.e., any antibiotic agent which contains a β-lactam nucleus in its molecular structure. Examples of penicillin derivatives include, e.g., oxacillin, nafcillin, cloxacillin, benzathine penicillin, penicillin G, penicillin V, procaine penicillin, methicillin, dicloxacillin, flucloxacillin, temocillin, amoxicillin, ampicillin, azlocillin, carbenicillin, ticarcillin, mezlocillin, and piperacillin. Examples of cephalosporins include, e.g., cefaclor, cefuroxime, cefamandole, cefotetan, cefoxitin, ceftriaxone, cefotaxime, cefpodoxime, cefepime, and cefpirome. An exemplary monobactam is, e.g., aztreonam, whereas an exemplary carbapenems include, e.g., imipenem, meropenem, ertapenem, and faropenem. Furthermore, exemplary beta-lactamase inhibitors include clavulanic acid, tazobactam, and sulbactam. In particular embodiments, the beta-lactam is a penicillin derivative or cephalosporin.

The present invention is also a method of screening drugs for activity to inhibit PBP4 activity in *S. aureus* isolates comprising contacting MW2 and/or USA300 isolates of *S. aureus* in vitro with a compound to be tested for activity against PBP4 and determining a MIC level for the compound and comparing the MIC level for the compound with an MIC level for oxacillin in MW2 and/or USA300 isolates. Compounds to be tested with this method would include any compound that is developed based either on chemical modification of cefoxitin or novel compounds found to bind to PBP4 based on a de novo drug or compound screen. These compounds are expected to inhibit growth of CA-MRSA in the presence of sub-MIC level of cefoxitin or other PBP4 inhibitors. In a particular embodiment, the compound is a derivative of cefoxitin, e.g., a derivative with additional or modified acetyl or amino groups, or additional side chains.

Once the efficacy of a drug or a combination of drugs has been shown based on the use of the in vitro screening method of the present invention, there are many different in vivo model systems that can be used by one of skill in the art to further demonstrate efficacy and aid in identification of doses that will be both safe and effective in humans. Such animal model systems are well-accepted and used during development of new human pharmaceuticals that will undergo scrutiny by various regulatory bodies worldwide and approved for use in humans. Examples of such model systems include but are not limited to a guinea pig model of *S. aureus* wound infection (Kernodle, D. S. and A. B. Kaiser. 1994. *Antimicrob. Agents Chemother.* 38:1325-1330); a rabbit model of *S. aureus* abscess in rabbits (Fernandez et al. 1999. *Antimicrob. Agent Chemother.* 43:667-671); a mouse model of *S. aureus* skin infection (Gisby, J. and J. Bryant. 2000. *Antimicrob. Agents Chemother.* 44:255-260); a mouse model of deep dermal *S. aureus* infection (Godin et al. 2005. *J. Antimicrob. Chemother.* 55:989-994); and a mouse intraperitoneal infection model (Patel et al. 2004. *Antimicrob. Agents Chemother.* 48:4754-4761). In such models, drugs can be tested against infections where the infection established is from inoculation of the animal with specific CA-MRSA strains. Demonstration of efficacy in such models is measured in many ways and would include but not be limited to a reduction in mortality rate, a reduction in bacterial cell counts determined by microscopic examination of tissue or blood samples taken from the animals, or even assessment of wound healing in the animals.

The efficacy of a drug that has been screened in vitro and shown to have activity to inhibit growth of CA-MRSA isolates will be further examined using the model described by Patel et al. (2004. *Antimicrob. Agents Chemother.* 48:4754-4761). Briefly, Swiss mice (6 mice per dose group, 4 weeks of age) will be inoculated intraperitoneally (i.p.) with 0.5 ml of bacterial suspension so that each mouse will receive from $2 \times 10^8$ to $3 \times 10^8$ CFU of CA-MRSA isolate. The drug to be tested, or the combination of drugs to be tested, is then at a dose shown to be effective in vitro but also known to be safe in animals. The doses to be tested are routinely chosen by those of skill in the art by using clinical judgment based on results of in vitro pharmacological assays. For example, doses can be ones that are equivalent to an $ED_{10}$, an $ED_{25}$, an $ED_{50}$, and an $ED_{75}$ for inhibiting bacterial growth in vitro. The drug will be administered at 1 and 4 hours after i.p. inoculation of mice with CA-MRSA isolates. The drug to be tested can be administered subcutaneously, intravenously, or orally. A vehicle control group will be used. All mice are observed for survival up to 7 days. Efficacy of the test drug will be measured as an increased survival rate as compared to control animals (untreated) and as compared to survival in a group of animals administered a positive control agent (e.g., vancomycin or another antibiotic known to have efficacy to treat CA-MRSA).

A mouse model of *S. aureus* skin infection (e.g. Godin et al. 2005. *J. Antimicrob. Chemother.* 55:989-994) will be used to examine the efficacy of a drug that has been screened in vitro and shown to have activity to inhibit growth of CA-MRSA isolates. Briefly, 4 to 5 week old immunocompetent ICR male mice will be used. Three groups of 18 mice each will be inoculated intracutaneously with CA-MSRA isolates. The intracutaneous injections will be applied to the back of each animal that will have been previously shaved with clippers. Six mice from each group will be inoculated with 0.1 ml of saline containing $10^7$, $10^8$ or $10^9$ CFU/ml of CA-MRSA isolate. The mice are then examined daily for development of deep dermal abscesses, inflammatory reaction in the inoculated area and wound size for a total of 3 weeks. The drug to be tested for antibiotic activity can be given orally, by intravenous injection or dermally. If dermal administration is to be tested, the drug will be spread over the area of the abscess. The dose of test drug to be administered will be chosen based on the results of in vitro studies of inhibition of bacterial growth. As discussed above, doses can be chosen based on the percentage of growth inhibition seen in vitro. The test drug will be administered 72 hours after intracutaneous injection with CA-MRSA inoculates and can last for 7 days or longer depending on the response of the animals to the treatment. At the end of 7 days treatment, animals will be sacrificed and the skin area corresponding to the infection site and underlying tissues can be processed for bacterial count and histopathological examination. Alternatively, mice can be sacrificed at various times, at least 3 mice per time period, such as 1, 3, and 7 days in order to monitor the progression of infection in response to the test drug.

It is contemplated that one of skill in the art will choose the most appropriate in vivo model system depending on the type of drug product being developed. Some in vivo models are more amenable to oral or intravenous injection while others are more desirable for dermal application methods. The medical literature provides detailed disclosure on the advantages and uses of a wide variety of such models.

Once a test drug or a combination of drugs has shown to be effective in vivo in animals, clinical studies can be designed based on the doses shown to be safe and effective in animals. One of skill in the art will design such clinical studies using standard protocols as described in textbooks such as Spilker (2000. *Guide to Clinical Trials*. Lippincott Williams & Wilkins: Philadelphia).

One particular type of composition that is contemplated by the present invention is a topical composition for treatment of CA-MRSA skin infections. Currently marketed topical antibiotics may contain multiple ingredients to target different types of pathogens in one product. However, such compositions are not effective against CA-MRSA. Based on the findings of the present invention, such multiple ingredient formulations could be developed wherein one component consists of the compositions of the present invention which have been shown to be effective against CA-MRSA. For example, on composition contemplated by the present invention would include but not be limited to a combination of bacitracin, polymyxin B, oxacillin, and cefoxitin. Also contemplated by the present invention would be a similar combination product that includes any identified PBP4 inhibitor plus β-lactams. Topical compositions are well known to those of skill in the art and would include the active drug ingredients formulated in pharmaceutically acceptable vehicles suitable for topical application to the skin. Such compositions can take the form of an ointment, cream, lotion, paste, gel, spray, aerosol, oil, wound dressing, or other pharmaceutical formulation which accomplishes direct contact between the active agent of the composition of the present invention and the skin. Topical formulations can also be prepared which are suitable for occlusive therapy.

Formulations in the forms of ointments, creams, lotions and pastes can generally have carriers in the forms of oleaginous bases (e.g., White Petrolatum and White Ointment); absorption bases formed by adding a water-in-oil emulsifying agent to an oleaginous base (e.g., Hydrophilic Petrolatum, AQUABASE, and AQUAPHOR); water-in-oil emulsion bases, prepared by adding water to an absorption base (e.g., HYDROCREAM, EUCERIN, NIVEA, and Cold Cream); oil-in-water emulsion bases (e.g., DERMABASE, UNIBASE, VELVACHOL, and hydrophilic ointment); and water soluble bases (e.g., polyethylene glycol ointment such as PEG 400-600 G or PEG 3350-400 G). Suitable carriers to produce a spray, gel, or aerosol are well-known in the art.

A carrier for topical application can also contain additional ingredients such as other carriers, moisturizers, humectants, emollients, dispersants, radiation blocking compounds, cleansing agents, anti-infective agents (e.g., antibiotics, fungicides, scabicides, or pediculicides), anti-inflammatory agents (e.g., corticosteroids), keratolytics (agents that soften, loosen, and facilitate exfoliation of the squamous cells of the epidermis), as well as other suitable materials that do not have a significant adverse effect on the activity of the topical composition. Additional ingredients can include, for example a sodium acid phosphate moisturizer, witch hazel extract, glycerine humectant, apricot kernal oil emollient, or corn oil dispersant. Other materials which can optionally be included in a topical composition include inositol or B-complex vitamins.

In one embodiment, a topical formulation containing an active agent of the present invention and a pharmaceutically acceptable carrier further contains transdermal or skin penetrant enhancers. Alternatively, the pharmaceutically acceptable carrier is a skin penetrant enhancer. Suitable skin penetrant enhancers include, but are not limited to, solvents such as water, alcohols (e.g., methanol, ethanol, 2-propanol), alkyl methyl sulfoxides (e.g., dimethylsulfoxide, decylmethyl sulfoxide, tetradecyl methyl sulfoxide), pyrrolidones (e.g., 2-pyrrolidone, N-methyl-2-pyrrolidone, N-(2-hydroxyethyl)pyrrolidone), laurocapram (AZONE), and other solvents such as acetone, dimethyl acetamide, dimethyl formamide, tetrahydrofurfuryl alcohol; amphiphiles such as anionic surfactants (e.g., docusate sodium, sodium lauryl sulfate), cationic surfactants (e.g., quaternary ammonium salts), amphoteric surfactants (e.g., lecithins, cephalins, alkylbetamines), nonionic surfactants (mono-, di-, and triglycerides), and other fatty acids and alcohols (e.g., lauryl, cetyl, and stearyl alcohols), sucrose, sorbitan and PEG; urea and N,N-dimethyl-m-toluamide.

Formulations suitable for transdermal administration can be presented as discrete patches adapted to remain in intimate contact with the epidermis of the recipient for a prolonged period of time. There are two basic designs of the patch system that dictate release characteristics of the active agent and patch behavior: (i) matrix or monolithic and (ii) reservoir or membrane. In the matrix system, the inert polymer matrix binds with the active agent and controls its release from the device. In the reservoir system, the polymer matrix does not control release of the active agent. Instead, a rate-controlling membrane present between the drug matrix and the adhesive layer provides the rate-limiting barrier for release of the active agent from the device. It is contemplated that either patch system is suitable for delivery of an active agent disclosed herein. Formulations suitable for transdermal administration can also be delivered by iontophoresis (see, for example, *Pharmaceutical Research* 3 (6):318 (1986)) and typically take the form of an optionally buffered aqueous solution of the compound. Suitable formulations contain citrate or bis\tris buffer (pH 6) or ethanol/water and contain from 0.1 to 0.2 M of the compound.

For the specific case of topical compositions examples of model systems include but are not limited to a guinea pig model of *S. aureus* wound infection (Kernodle, D. S. and A. B. Kaiser. 1994. *Antimicrob. Agents Chemother.* 38:1325-1330); a rabbit model of *S. aureus* abscess in rabbits (Fernandez et al. 1999. *Antimicrob. Agent Chemother.* 43:667-671); a mouse model of *S. aureus* skin infection (Gisby, J. and J. Bryant. 2000. *Antimicrob. Agents Chemother.* 44:255-260); and a mouse model of deep dermal *S. aureus* infection (Godin et al. 2005. *J. Antimicrob. Chemother.* 55:989-994). All of these models are applicable to testing topical compositions such as the compositions of the present invention. In such animal models, the drugs tested are formulated in vehicles such as those described above and used in human drug products. Using such models, drugs can be tested against infections where the infection established is from inoculation of the animal with specific CA-MRSA strains. Demonstration of efficacy in such models is measured in many ways and would include but not be limited to a reduction in mortality rate, a reduction in bacterial cell counts determined by microscopic examination of tissue or blood samples taken from the animals, or even assessment of wound healing in the animals.

The following non-limiting examples are provided to further illustrate the present invention.

EXAMPLES

Example 1

Bacterial Strains and Culture Conditions

The *E. coli* strain XL-1 blue was used in molecular cloning experiments. Luria-Bertani medium (Becton Dickinson) was used for culture of *E. coli* while *S. aureus* was cultured in Mueller Hinton Broth (Becton Dickinson) supplemented with 25 µg/ml $Ca^{2+}$, 12.5 µg/ml $Mg^{2+}$ and 2% NaCl (designated CSMHB). When appropriate, antibiotics were added to the media at the following concentrations: ampicillin at 100 µg/ml for *E. coli*; chloramphenicol at 10 µg/ml and erythromycin at 2.5 µg/ml for *S. aureus*. Chloramphenicol was routinely used to maintain selection for pEPSA5- and pSK236-based plasmids (Forsyth, et al. (2002) *Mol. Microbiol.* 43:1387). All antibiotics were obtained from Sigma (St. Louis, Mo.).

Example 2

DNA and Computational Techniques

Plasmid DNA was isolated by standard techniques (QIAGEN, Valencia, Calif.) from *E. coli* and from lysostaphin digest of *S. aureus*. Chemically-competent *E. coli* or electrocompetent *S. aureus* was used for transformation. New England Biolab restriction endonucleases and ligases were used according to the manufacturers' recommendations. IPROOF DNA polymerase from BIO-RAD was used according to the manufacturers' recommendations to generate all DNA fragment for deletions, promoter fusions, and ectopic expressions in pEPSA5. Fidelity of all DNA sequences generated by PCR was verified using fluorescently-labeled dideoxynucleotides (BIG DYE™ terminators; PE Applied Biosystems) in DNA sequencing reactions.

Example 3

Construction of S. aureus Mutants

All mutants were generated with in-frame deletion of target genes by allelic replacement, using the temperature-sensitive plasmid pMAD. Briefly, ~0.8 kb PCR products upstream and downstream of targeted sequences were generated and ligated by gene SOEing (Horton, et al. (1990) *Biotechniques* 8:528). The resulting ~1.6 kb product was digested, gel purified with QIAGEN columns, inserted into pMAD using same restrictions sites and transformed into *E. coli*. Colony PCR was performed on *E. coli* transformants and positive clones were then grown in media supplemented with antibiotic. Plasmids were isolated from *E. coli*, verified by digestion analysis and then used to transform *S. aureus* RN4220, selecting for erythromycin or chloramphenicol resistant and blue colonies at 30° C. Plasmid from 4220 was sequenced and used to transform *S. aureus* strains MW2, COL, USA300, N315 and Mu50 for which the gene was to be deleted. The process of allelic replacement is well-known in the art (Arnaud, et al. (2004) *Appl. Environ. Microbiol.* 70:6887). For Mu50, N315 and USA300 which are erythromycin resistant, a modified pMAD vector was constructed (pMAD-CM) by cloning the chloramphenicol acetyltransferase (cat194) gene from pSK236 into the NaeI site of pMAD. For each in-frame deletion mutant strain, the chromosomal deletion was verified by PCR and DNA sequencing. A minimum of three independent clones for each mutant were generated in every genomic background analyzed and then utilized for further testing. The resulting deletion strains were devoid of the entire ORF for both pbp3 and pbp4. The same pMAD system was utilized to reinsert the pbp4 ORF into the MW2 Δpbp4 and Δpbp3/4 and the USA300 Δpbp4 for complementation.

Example 4

Isolation of RNA and Northern Blot Hybridization

Overnight cultures of *S. aureus* were diluted 1:100 in 40 mL of CSMHB broth and grown with shaking to exponential phase (A650 nm=0.7) in 200 mL flasks. At OD 0.7 (Spectronic 20 using 18-mm borosilicate glass tubes), total RNA was extracted from 10 mL of culture while remaining 30 mL were divided evenly to 3 glass tubes, one with no antibiotic, the second with 10×MIC oxacillin and the third with 10×MIC vancomycin. Bacterial cultures were then left growing for an additional 60 minutes. RNAs from all samples were extracted by using a TRIZOL-glass bead method known in the art (Manna et al. (2004) *J. Bacteriol.* 186:5267). The concentration of total RNA was determined by measuring the absorbance at 260 nm. Ten micrograms each of total RNA was analyzed by Northern blot analysis. Each DNA probe (350 bp) was generated by PCR from chromosomal templates. For detection of specific transcripts, gel-purified DNA probes were radiolabeled with [$\alpha$-32P]-dCTP by using the random-primed DNA labeling kit (Roche Diagnostics GmbH), and hybridized under aqueous phase conditions at 65° C. The blots were subsequently washed and bands visualized by autoradiography.

Example 5

Transcriptional Fusion Studies of PBP2 Promoters Linked to the GFP$_{uvr}$ Reporter Gene To confirm the effect of the pbp4 mutation on pbp2, both pbp2 promoters were cloned in pALC1484, a derivative of pSK236 containing the promoterless gfp$_{uvr}$ gene to generate transcriptional fusions. Clustal W was utilized to align the promoter sequences from HA-MRSA strain COL and the CA-MRSA strain MW-2, and showed the sequences to be 100% identical. Restriction analysis and DNA sequencing confirmed the orientation and authenticity of the promoter fragments upstream of the reporter gene. Recombinant plasmids were introduced into *S. aureus* RN4220, purified and electroporated into wild-type MW2, COL and their isogenic pbp mutants. Overnight cultures were diluted 1:100 in CSMHB with chloramphenicol and grown to an OD$_{650}$ of 0.7; bacterial cultures were then exposed for 60 minutes to no antibiotic, oxacillin or vancomycin at 10×MIC. Aliquots of 200 μl were transferred before antibiotic challenge and every hour thereafter to microtiter wells to assay for cell density (OD$_{650}$) and fluorescence in a FL600 fluorescence reader (BioTek Instruments). Promoter activation was plotted as mean fluorescence/OD$_{650}$ ratio, using the average values from triplicate readings from three clones per strain.

Example 6

Ectopic Expression of Genes in S. aureus

To complement the mutant strains, pMAD and the pEPSA5 expression plasmid were utilized. The same cycling utilized for generating the mutants was used with pMAD to reinsert the pbp4 gene into pbp4 and pbp3/4 mutants of MW2 and pbp4 mutant of USA300. As far as pEPSA5, genes were amplified by PCR and products were digested, gel-purified and ligated into pEPSA5. After transformation into *E. coli* XL-1 BLUE, colony PCR was performed on *E. coli* transformants and plasmid from positive clones were isolated from *E. coli*, verified by digestion analysis and then used to transform first in *S. aureus* RN4220. The positive plasmids were then introduced into MW2, USA300 and their isogenic pbp4 mutants as described above. To further confirm correct induction of each transcript with 1% xylose, RT-PCR was performed on RNAs prior and after xylose induction. Briefly, total RNA was extracted and resuspended in DEPC water. Each RNA sample was then treated with Turbo DNase from Ambion and c-DNA was generated from 1 μg of total RNA, using the Transcriptor First Strand cDNA Synthesis Kit (Roche). Regular PCR was then performed on c-DNAs using oligonucleotides specific for each gene. Genes cloned into pEPSA5 can be induced for expression with xylose (1%) or repressed by glucose (1%); however a basal level of expression was always observed without adding exogenous xylose to culture media.

Example 7

TRITON X-100-Induced Autolysis Assays in Static Cultures

The autolysis assay was performed according to established methods (Ingavale, et al. (2003) *Mol. Microbiol.* 48:1451). Briefly, strains grown overnight in TSB were diluted and grown to mid-logarithmic phase (A650 nm=0.7). Cells were washed twice in cold sterile distilled water and resuspended in 10 ml of 0.05 M Tris-HCl pH 7.2 containing 0.05% TRITON X-100. Cells were incubated at 30° C. and A600 nm was measured every thirty minutes. Data are expressed as percent loss of A600 nm at indicated times

Example 8

Effect of TRITON X-100 on Growing Cells

The effect of the non-ionic surfactant TRITON X-100 was assayed on actively dividing cells according to established methods (Ingavale et al. 2003. *Mol. Microbiol.* 48:1451). Briefly, overnight cultures were diluted to an OD650 of 0.1 in CSMHB with different concentrations of TRITON X-100. Cells were incubated at 37° C. with shaking, and optical densities were recorded hourly for 7-8 hours. Each data point represents the mean and standard deviation from three independent experiments.

Example 9

Zymogram Assay

Zymogram analysis was conducted to detect alterations in autolysin activity as previously described with minor alterations (Ingavale et al. 2003. *Mol. Microbiol.* 48:1451). Heat-killed RN4220 cells were incorporated into an 8% SDS-PAGE gel at 10 mg/ml wet weight. Autolytic enzymes were extracted from 10 ml of culture grown to A650 nm=0.7 using 100 µl of 4% SDS and equivalent protein levels were loaded onto the SDS-PAGE gel. After proteins were renatured overnight in water, the gel was incubated with 0.1% methylene blue to visualize clear bands, representing an area of RN4220 cell lysis. The assay was repeated three times with a representative experiment shown.

Example 10

Electron Microscopy

Overnight cultures were re-inoculated in fresh CSMHB and grown to an $OD_{650}$ of 0.7. One 1 mL aliquot was harvested by low-speed centrifugation and fixed immediately with 2% glutaraldehyde/1% paraformaldehyde. Oxacillin was then added to the other two specimens to achieve a final concentration of 1×MIC and 10×MIC, with cells growing at 37° C. for an additional 60 minutes. All specimens were then harvested and fixed accordingly. After being washed three times with sodium cacodylate buffer, cells were post-fixed with $OsO_4$ and washed again. Cells were subsequently dehydrated through an ethanol series including en-block staining with 2% aqueous uranyl acetate. Samples were then embedded in EMBED-812 resin over propylene oxide; polymerization was performed at 60° C. for 48 hours. Ultra-thin sections were obtained with glass knives, and post-stained with 2% methanolic uranyl acetate and lead citrate. The sections were then examined with a JEOL JEM 1010 Electron Microscope, equipped with an AMT bottom-mounted high resolution digital imaging CCD camera system. All reagents for Electron Microscopy were bought from Electron Microscopy Sciences (Hatfield, Pa., USA).

Example 11

Analysis of Peptidoglycan

Peptidoglycan, muropeptides preparation and consequent HPLC separation, was performed according to known methods (de Jonge et al. 1992. *J. Biol. Chem.* 267:11248). Briefly, cell wall extracts were purified by shaking bacteria with glass beads and by enzymatic digestion of DNA, RNA and proteins. Peptidoglycan was then obtained by treating cell wall extracts with hydrofluoric acid. Muropeptides obtained by digesting peptidoglycan with mutanolysin (Sigma) were separated by HPLC and detected by absorption at 206 nm. Quantification was made by measuring the area of each individual peak and expressing it as a percentage of the total area of all peaks. Peaks of interest were desalted and analyzed by MALDI-MS using yano-4-hydroxycinnamic acid as the MALDI matrix at the MS Service in ITQB, Lisbon.

Example 12

Collection of Clinical Isolates and Fast Screening of CA-MRSA Versus HA-MRSA Strains Two independent batches of clinical isolates were obtained from the Dartmouth Hitchcock Medical Center, Lebanon, N.H. The first group included 200 blood MRSA isolates sub-cultured on 5% Columbia sheep blood agar (Remel). The second group involved 30 MRSA isolates from complicated skin and soft tissue infections (CSSTI) similarly sub-cultured. All strains were grown overnight in CSMHB broth and streaked on selective mannitol salt agar plates for confirmation. DNA extraction was performed on 500 µl of cultures. PCR was performed on all DNAs with oligonucleotides specific for mecA, pvl and the four genes found to be specific for the SCCmec type IV in CA-MRSA: MW0042, MW0043, MW0046, and MW0047. DNA amplification of mecA was used as a control to confirm that all strains were MRSA. DNAs from *S. epidermidis*, *E. coli* and *S. pneumoniae* were used as negative controls to confirm the specificity of the oligonucleotides. After amplification for 30 cycles (5 min of denaturation at 95° C., 30 s of annealing at 54° C. and 1 min extension at 72° C.), PCR products were resolved by electrophoresis through 1.5% agarose gels stained with ethidium bromide. Given the number of clinical isolates tested, only a small random group of PCR products were subjected to DNA sequencing to confirm specificity. *S. aureus* strain COL, Mu50, N315 and MRSA252 all tested negative for all MW0042, MW0043 and MW0047 and pvl while USA300 and MW2 were positive controls for this PCR reaction. The primer sequences for mecA, MW0042, MW0043 and MW0047 were as follows: mecA-UP 5'-GGT ACT GCT ATC CAC CCT CAA A-3' (SEQ ID NO:19), mecA-LOW 5'-TTA CGA CTT GTT GCA TAC CAT CA-3' (SEQ ID NO:20), MW0042-UP 5'-ATT GGC AGA AAT AAA CAA AAC G-3' (SEQ ID NO:21), MW0042-LOW 5'-TCG TTT AAT TTT TTC CCA AAC TC-3' (SEQ ID NO:22), MW0043-UP 5'-GTT TCA GTT GGT GTT GAA GAT CC-3' (SEQ ID NO:23), MW0043-LOW 5'-CCT ATA ATT TTC GAT AGA TTC GTG-3' (SEQ ID NO:24), MW0047-UP 5'-AGG CAT ATA AAG AAG CAG GAA AG-3' (SEQ ID NO:25), MW0047-LOW 5'-CAC ACT GTT TTC CTA CGA TAT TTG-3' (SEQ ID NO:26).

Example 13

Susceptibility Testing and Synergy Assay

Minimum inhibitory concentrations and minimum bactericidal concentrations (MIC and MBC, respectively) were determined for each isolate in triplicate by microdilution techniques with an inoculum of $5 \times 10^5$ CFU/ml according to the Clinical and Laboratory Standards Institute guidelines. Aliquots (5 µl) from clear wells were plated onto TSA drug-free plates for the determination of MBCs, followed by incubation at 37° C. for 24 and 48 hours. For the mutant strains, each one of the three clones was tested. MIC data were reported as median values from at least three independent experiments for each antibiotic. Also, strains containing pEPSA5-based plasmids were tested with and without xylose induction, but chloramphenicol was not added to avoid interference with beta-lactam resistance evaluation. To assess the synergistic effect of cefoxitin plus oxacillin, the MIC for cefoxitin for both CA- and HA-MRSA strains was determined first; 0.25×MIC of cefoxitin were then used in combination with a two-fold dilution of oxacillin to ascertain their synergistic effect. The correct inocula were confirmed by plating serial dilutions on agar. The synergistic inhibitory activity of cefoxitin with oxacillin was scored at 24 and 48 hours. Cefuroxime, a β-lactam with very low affinity for PBP4, was also tested in combination with two-fold dilutions of oxacillin and was found to have no effect whatsoever on oxacillin MICs; this finding reinforces the specificity of the interaction between cefoxitin and oxacillin.

Example 14

Population Analysis

Antibiotic susceptibilities for MW2 were also determined by population analysis (Tomasz, A. et al. 1991. *Antimicrob. Agents Chemother.* 35:124-129). Briefly, the cells were grown overnight in CSMHB at 37° C., and then four different dilutions of the bacterial culture ($10^0$, $10^{-2}$, $10^{-4}$, and $10^{-6}$) were plated on control plates without antibiotic and on plates which contained a series of two-fold dilutions of the cefoxitin, oxacillin or oxacillin combined to one fourth the MIC of cefoxitin. The plates were incubated at 37° C. for 48 h, and colonies were counted.

What is claimed is:

1. A topical composition for treating a CA-MRSA infection in a patient consisting of an effective amount of cefoxitin and an effective amount of oxacillin in a pharmaceutically acceptable vehicle, wherein said vehicle is suitable for topical application to the skin of a patient with a CA-MRSA infection, and further wherein said vehicle is White Petrolatum.

2. The topical composition of claim 1 wherein the CA-MRSA infection is with an MW2 strain or a USA300 strain.

3. The topical composition of claim 1 wherein pharmaceutically acceptable vehicle is formulated as an ointment, a cream, a lotion, a paste, a gel, a spray, an aerosol, an oil, or a wound dressing.

* * * * *